US012733798B2

(12) United States Patent
Christensen

(10) Patent No.: US 12,733,798 B2
(45) Date of Patent: Sep. 15, 2026

(54) ENDOSCOPE COMPRISING A DOUBLE BRAKE FOR UP-DOWN AND LEFT-RIGHT

(71) Applicant: AMBU A/S, Ballerup (DK)

(72) Inventor: Martin Johst Christensen, Copenhagen Ø (DK)

(73) Assignee: AMBU A/S, Ballerup (DK)

( * ) Notice: Subject to any disclaimer, the term of this patent is extended or adjusted under 35 U.S.C. 154(b) by 353 days.

(21) Appl. No.: 18/218,758

(22) Filed: Jul. 6, 2023

(65) Prior Publication Data

US 2024/0016369 A1 Jan. 18, 2024

(30) Foreign Application Priority Data

Jul. 13, 2022 (EP) .................................... 22184711

(51) Int. Cl.
*A61B 1/005* (2006.01)
*A61M 25/01* (2006.01)

(52) U.S. Cl.
CPC ....... *A61B 1/0052* (2013.01); *A61M 25/0136* (2013.01)

(58) Field of Classification Search
CPC .............. A61B 1/0052; A61B 1/00131; A61B 1/00071; A61B 1/0055; A61M 25/0136
See application file for complete search history.

(56) References Cited

U.S. PATENT DOCUMENTS

| | | | |
|---|---|---|---|
| 4,742,816 | A | 5/1988 | Suzuki et al. |
| 5,014,685 | A | 5/1991 | Takahashi |
| 5,329,887 | A | 7/1994 | Ailinger et al. |
| 5,496,260 | A | 3/1996 | Krauter et al. |
| 5,507,717 | A | 4/1996 | Kura et al. |
| 6,656,111 | B2 | 12/2003 | Fujii et al. |
| 6,673,012 | B2 | 1/2004 | Fujii et al. |
| 7,856,089 | B2 | 12/2010 | Hanna |
| 8,608,649 | B2 | 12/2013 | McWeeney et al. |
| 2001/0034472 | A1 | 10/2001 | Fujii et al. |
| 2007/0255104 | A1 | 11/2007 | Maruyama |
| 2011/0088498 | A1 | 4/2011 | Ettwein et al. |

(Continued)

FOREIGN PATENT DOCUMENTS

| | | |
|---|---|---|
| WO | 2021007204 A1 | 1/2021 |

OTHER PUBLICATIONS

Extended search report in related European Application No. 22184711.4, dated Dec. 7, 2022, 7 pages.

*Primary Examiner* — Michael J Carey
(74) *Attorney, Agent, or Firm* — Faegre Drinker Biddle & Reath LLP

(57) ABSTRACT

An endoscope including: a handle or interface and an insertion cord including a bending section. The endoscope handle or interface includes a first operation unit having a first manually operable element, which when rotated by an operator causes bending of the bending section in a first bending plane; a second operation unit having a second manually operable element, which when rotated by the operator causes bending of the bending section in a second bending plane; and a manually operable brake activator which is configured to activate braking or locking both a rotation of the first manually operable element via an engagement of a first brake part with the first operation unit and a rotation of the second manually operable element via an engagement of a second brake part with the second operation unit.

20 Claims, 9 Drawing Sheets

(56) References Cited

U.S. PATENT DOCUMENTS

| | | | | |
|---|---|---|---|---|
| 2011/0213300 | A1* | 9/2011 | McWeeney | A61B 6/06 604/95.04 |
| 2012/0277535 | A1 | 11/2012 | Hoshino | |
| 2014/0088497 | A1 | 3/2014 | Campbell et al. | |
| 2014/0343489 | A1 | 11/2014 | Lang et al. | |
| 2015/0045621 | A1 | 2/2015 | Masaki | |
| 2015/0173746 | A1 | 6/2015 | Baxter, III et al. | |
| 2015/0359415 | A1* | 12/2015 | Lang | A61M 25/0147 600/141 |
| 2018/0028048 | A1* | 2/2018 | Simmons | A61M 25/0105 |
| 2021/0338049 | A1 | 11/2021 | Christensen | |
| 2021/0338050 | A1 | 11/2021 | Christensen et al. | |
| 2021/0338051 | A1 | 11/2021 | Nielsen et al. | |
| 2022/0151463 | A1 | 5/2022 | Fancher et al. | |
| 2023/0042893 | A1 | 2/2023 | Golden et al. | |
| 2023/0148844 | A1 | 5/2023 | Christensen et al. | |
| 2023/0172429 | A1 | 6/2023 | Schütz et al. | |
| 2023/0248212 | A1 | 8/2023 | Quensel et al. | |

* cited by examiner 26
66
90
60
30
70
92
62
32
38

ENDOSCOPE COMPRISING A DOUBLE BRAKE FOR UP-DOWN AND LEFT-RIGHT

CROSS-REFERENCE TO RELATED APPLICATIONS

This application claims priority from and the benefit of European Patent Application No. EP 22184711.4, filed Jul. 13, 2022, which is incorporated by reference herein in its entirety.

TECHNICAL FIELD

The present disclosure relates to an endoscope. More specifically, the disclosure relates to a braking mechanism for braking a four-way bending endoscope.

BACKGROUND

Endoscopes, including procedure specialized endoscopes such as bronchoscopes, arthroscopes, colonoscopes, laparoscopes, gastroscopes, duodenoscopes, cholangioscopes and ureteroscopes, are used for visual examination and diagnosis of hollow organs and body cavities, as well as to assist in surgery, e.g. for a targeted tissue sampling. Reusable endoscopes require cleaning and sterilization while single-use endoscopes are discarded rather than cleaned. Known endoscopes usually comprise an endoscope handle via which an operator/user can hold and control the endoscope, and an insertion cord comprising an insertion tube, an actively bendable bending section, and a distal tip that contains a light emitting device and an imaging device comprising e.g. an image sensor and a lens system so that the patient's body cavity can be illuminated and viewed by the operator/user, e.g. via a monitor connected to the endoscope.

Two-way bending endoscopes are configured to enable bending of the actively bendable bending section in one bending plane, e.g. in up-down direction. Four-way bending endoscopes are configured to enable bending of the actively bendable bending section in two bending planes, e.g. in both up-down direction and left-right direction. Known four-way bending endoscopes e.g. comprise a first operation unit and a second operation unit, wherein each operation unit comprises a manually operable element like a lever or a (handle) wheel connected to a wire drum or pulley, to which steering wires or steering wire portions are connected. When the manually operable element is rotated by an operator, the manually operable element and the respective wire drum or pulley connected to the same rotate integrally with each other. The rotation of the respective operation unit formed by at least the manually operable element and the wire drum or pulley is transmitted into a pulling or releasing movement of the steering wires, which effects the bending movement of the bending section. Each operation unit has its own manually operable brake activator, via which each operation unit may be independently braked or locked.

Thus, it is possible to suitably apply a braking or locking force onto the respective operation unit so that movement of the bending section in the bending plane in which the respective operation unit enables bending is locked or braked. For some endoscope types, it may however not be necessary to independently brake or lock each operation unit and/or it may be the case that brake force requirements are rather low. An example of such endoscope types are cholangioscopes or baby endoscopes (miniature endoscopes), which are provided to be used together with a mother endoscope. For such endoscopes and potentially for other endoscope types it may be acceptable to provide one manually operable brake activator which is configured to activate braking or locking both a rotation of the first operation unit and a rotation of the second operation unit.

A cholangioscope or baby endoscope (miniature endoscope) is attached to a mother endoscope via an attachment device like a strap. The cholangioscope is a four-way-bending endoscope. In use, an insertion cord of the cholangioscope is inserted into a working channel of the mother endoscope. The cholangioscope has a steering mechanism enabling the four-way bending. Two control knobs or wheels are provided, which are attached to pulleys or wire drums, and a rotational movement of the control knobs is transmitted to steering wires connected to the pulleys for effecting a bending movement of the bending section. A lock or brake mechanism is provided via which the bending section can be locked in a desired deflected position during use. The lock mechanism comprises a lock lever that is actuatable between a locked position and an unlocked position. When the lever is rotated, a lever member having a cam profile rotates together with the lever. The cam profile of the lever member engages with a cam profile of a pulley member such that a rotational movement of the lever and the lever member is transmitted into a translational movement of the pulley member. This translational movement of the pulley member causes the pulleys or wire drums to be frictionally engaged between a housing of the handle and a thrust plate or between the thrust plate and the pulley member, so that the rotations of the pulleys are locked. O-rings are provided, which function as friction elements when the pulleys are frictionally engaged, and which function also as flexible elements pushing the pulleys away from the pulley member or from the housing when the lock lever is rotated from the locked position to the unlocked position. A squeaking noise is generated during activation of braking. Moreover, it has turned out that it is difficult to equally transfer locking or braking forces. Therefore, it is often necessary to apply a high force to guarantee that both pulleys are suitably locked in rotation, which is a disadvantage of such braking mechanisms.

SUMMARY

The tasks and objectives of the present disclosure are to eliminate or at least to reduce the disadvantages of the related art. More specifically, the problem addressed by the present disclosure is how to brake bending movement of the bending section without excessive force and without generating undesirable noise.

Accordingly, a four-way bending endoscope shall be provided, which has a double brake of good quality enabling locking or braking of up-down rotation and left-right rotation with a common brake actuator.

In embodiments presented by the present disclosure, an endoscope comprises a manually operable brake activator which is configured to activate braking or locking both a rotation of a first operation unit via an engagement of a first brake part with the first operation unit and a rotation of a second operation unit via an engagement of a second brake part with the second operation unit.

The endoscope according to the present disclosure is preferably a low-cost, lightweight, single-use endoscope, which is intended to be disposed after use in a single patient. This means that the endoscope is preferably optimized for one single use. The endoscope preferably has a limited number of elements, which are preferably manufactured with a low-cost material (polymer/plastic/resin) in preferably a low-cost manufacturing process (plastic/injection moulding) and which can be easily assembled.

The endoscope according to the present disclosure is, for example, a cholangioscope or an ureteroscope. However, the present disclosure is not limited to cholangioscopes or ureteroscopes. In particular, the endoscope according to the present disclosure may be another specialized four-way endoscope.

Preferably, the endoscope also comprises handle or interface; and an insertion cord configured to be inserted into a patient's body cavity and comprising an actively bendable bending section; the endoscope handle or interface comprising: the first operation unit, which when rotated by an operator causes a bending of the actively bendable bending section in a first bending plane; and the second operation unit, which when rotated by the operator causes a bending of the actively bendable bending section in a second bending plane. The bending section may comprise a plurality of bending segments being connected via hinges. The bending section may be injection molded as a one-piece part with hinges formed between adjacent segments.

Said differently, the present disclosure provides a double brake for up-down and left-right, i.e. a lock or brake mechanism via which both up-down rotation and left-right rotation can be simultaneously braked or locked. Two brake parts—the first brake part and the second brake part—are provided, and an actuation or operation of the provided (one/single) brake activator leads to an engagement of the first brake part with the first operation unit and to an engagement of the second brake part with the second operation unit. In other words, there is a first specific engagement between the first brake part and the first operation unit leading to a braking or locking of the rotation of the first operation unit and a second specific engagement between the second brake part and the second operation unit leading to a braking or locking of the rotation of the second operation unit. By braking it is meant that the engagement of the brake parts with the operation units generates forces that constrain movement of the operation units and thus constrain articulation of the bending section. Braking is simultaneous when the forces (e.g. friction) that brake the two operation units occur at the same time, and this understanding permits one of the forces to cause braking before the other so long as both brake at the same time at some point in time. Simultaneous braking also permits one of the forces to be greater than the other. As described below, the amount of constrain should suffice to prevent accidental rotation of the operation units. However, the amount of constrain can be designed to allow, while braking, an operator to fine-tune the position of the bending section or to allow the bending section to straighten when removed from the patient. Thus, a first amount of force is necessary to rotate the operation units without braking, and a second amount (greater than the first) is necessary to overcome braking. The first and second amounts can be different for each operating unit. The first amount overcomes friction inherent in the construction of the handle and insertion cord.

Using the individual braking or locking engagements between the brake parts and the operation units has turned out to be advantageous compared to e.g. the squeezing or sandwiching of the wire drums/pulleys between a housing of the endoscope handle, a pulley member and a thrust plate, using also two O-rings. The present disclosure thus provides a double brake activatable by one single manually operable brake activator, enabling simultaneous locking or braking of up-down rotation and left-right rotation, having a simple and compact design. The double brake may enable equal transfer of locking or braking forces, without generating squeaking noise during activation of the braking, leading to a rather high-quality impression on the user of the provided double brake. The solution according to the present disclosure further provides the benefit that much of the brake mechanics are arranged outside of the handle shell or housing, meaning that the handle can be made relatively compact, which is of particular advantage for small endoscopes, such as cholangioscopes and ureteroscope It is to be understood that "proximal" means close to an operator and away from a patient and "distal" means away from the operator and close to the patient according to the present disclosure.

Preferably, the first bending plane is perpendicular to the second bending plane. E.g. bending of the bending section in the first bending plane means a bending in a left-right direction, and bending of the bending section in the second bending plane means a bending in an up-down direction.

The endoscope according to the present disclosure is preferably a miniature endoscope or baby endoscope and has a rather small diameter.

The insertion cord of the endoscope preferably comprises an insertion tube, the actively bendable bending section and a distal tip unit extending in this order in the proximal-distal direction.

The first operation unit preferably comprises the first manually operable element and a first wire drum or pulley. The first operation unit may comprise the first manually operable element and the first wire drum or pulley. This has the advantage that the number of independent or separate parts of the first operation unit is preferably only two. With single-use endoscopes it is basically desirable to reduce the number of parts used to assemble the endoscope. However, the present disclosure is not limited to the first operation unit having only two parts. E.g., there may be provided a first shaft fixed to both the first manually operable element and the first wire drum or pulley.

The first manually operable element is e.g. a lever or a (handle) wheel. The first manually operable element may be a wheel. The first manually operable element is preferably fixed to the first wire drum such that the first manually operable element rotates integrally or together with the first wire drum. In case a first shaft is provided in addition to the first manually operable element and the first wire drum, the first manually operable element preferably rotates integrally or together with both the first shaft and the first wire drum. A rotation of the first manually operable element by the operator preferably leads directly to a rotation of the first wire drum and thus to a rotation of the entire first operation unit.

The second operation unit preferably comprises the second manually operable element and a second wire drum or pulley. The second operation unit may comprise the second manually operable element and the second wire drum or pulley. This has the advantage that the number of independent or separate parts of the second operation unit is preferably only two, thus enabling a reduction of the number of parts used to assemble the endoscope. However, the present disclosure is not limited to the second operation unit having only two parts. E.g., there may be provided a second shaft fixed to both the second manually operable element and the second wire drum or pulley.

The second manually operable element is e.g. a lever or a (handle) wheel. The second manually operable element may be a wheel. The second manually operable element is preferably fixed to the second wire drum such that the second manually operable element rotates integrally or together with the second wire drum. In case a second shaft is provided in addition to the second manually operable element and the second wire drum, the second manually operable element preferably rotates integrally or together with both the second shaft and the second wire drum. A rotation of the second manually operable element by the operator preferably leads directly to a rotation of the second wire drum and thus to a rotation of the entire second operation unit.

Steering wires or proximal steering wire portions are preferably connected to the first wire drum and to the second wire drum. The steering wires or distal steering wire portions are preferably connected to the bending section, in particular to a distal end of the bending section. Therefore, via a rotation of the first and second manually operable elements respectively the first and second operation units the bending movement of the bending section may be effected.

The first operation unit and the second operation unit are preferably arranged coaxially with respect to each other. The first manually operable element and the second manually operable element are preferably arranged outside with respect to a housing of the endoscope handle or interface. A radius of the first manually operable element is preferably smaller than a radius of the second manually operable element, which makes a distinction between the two manually operable elements easy for the operator. In particular, the operator can easily distinguish between the two manually operable elements even without looking. At least portions of the first wire drum and of the second wire drum to which the steering wires are connected are preferably arranged inside the housing of the endoscope handle or interface. In an axial direction the first manually operable element is preferably arranged next to the second manually operable element, wherein the second manually operable element is preferably closer to the housing of the endoscope handle or interface and the first manually operable element is preferably farther away from the housing of the endoscope handle or interface. Moreover, in an axial direction, preferably the portion of the first wire drum to which steering wires are connected is arranged next to the portion of the second wire drum to which steering wires are connected. Said portion of the second wire drum may be closer to the housing of the endoscope handle or interface, and said portion of the first wire drum is farther away from the housing of the endoscope handle or interface. The two operation units are therefore advantageously compactly designed and assembled and need little installation space in the endoscope handle or interface.

Preferably, the endoscope handle or interface further comprises a static base component, which is a part or component fixedly attached to a housing of the endoscope handle or interface. The static base component is preferably a static or stationary part, i.e. is immovable/immobile with respect to the housing of the endoscope handle or interface. The static base component may be an integral part, e.g. made from a polymer or plastic material, which is advantageous in order to keep the number of parts to be assembled to a minimum. However, the static base component may alternatively also be manufactured by assembling two or even more (polymer/plastic) parts.

The first operation unit and the second operation unit are preferably rotatably mounted on and connected or attached to the static base component. The static base component may have a cylindrical portion, or may at least in portions be formed cylindrically, and the cylindrical portion may be arranged coaxially with respect to the first operation unit and the second operation unit. The cylindrical portion may be hollow. In a radial direction, the cylindrical portion of the static base component may be arranged between the first operation unit and the second operation unit, so that the first operation unit is preferably rotatably mounted on a radially inner side of the cylindrical portion and the second operation unit is preferably rotatably mounted on a radially outer side of the cylindrical portion. The provision of the cylindrical portion of the static base component advantageously makes assembly of the first and second operation units, which are preferably also formed cylindrically at least in portions, into the endoscope handle or interface quite easy.

According to the present disclosure the manually operable brake activator is provided, which is configured to activate braking or locking both the rotation of the first operation unit and the rotation of the second operation unit. The brake activator preferably can be switched, in particular rotated, by the operator between a brake-on position and a brake-off position. It is to be understood that the brake-on position is a position of the brake activator, in which braking or locking the rotation of the first and second operation units is activated, and that the brake-off position is a position of the brake activator in which braking or locking the rotation of the first and second operation units is deactivated. Therefore, when the brake activator is in the brake-off position, bending of the bending section can be effected by the operator and the first and second operation units, in particular the first and second manually operable elements, may be freely rotated, i.e. without being locked or braked. When the brake activator is in the brake-on position, braking or locking the rotation of the first operation unit and of the second operation unit is activated, i.e. rotation of the first manually operable element and the second manually operable element is preferably restricted so that the bending section stays in position, remains in a braked state and may not be accidentally effected by the operator. However, the brake torque applied in the braked state is preferably limited so the operator would be able to fine-tune position of the bending section even in the brake-on position. A limited brake torque preferably also has the consequence that when the insertion cord of the endoscope is accidentally withdrawn from a patient with the bending section being in a bent configuration and with the double brake being activated, i.e. with the brake activator being in the brake-on position, the bending section may straighten out, thereby mitigating a potential risk of injuring the patient.

The brake activator may comprise a brake lever or brake lever portion, which is operable by the operator. The brake activator may be an integral part or component, made e.g. from a polymer or plastic material and manufactured e.g. in an (injection) molding process, which is advantageous in order to keep the number of parts to be assembled to a minimum. In this case the brake activator may be described as having a brake lever portion and an activation portion. However, the brake activator may alternatively also be assembled by two or even more (polymer or plastic) parts. E.g. there may be provided a brake lever and a separate activation part connected, in particular fixedly attached, to each other, wherein the brake lever and the activation part together form the brake activator.

The brake activator preferably has a cylindrical portion, which is preferably provided at or forms (at last part of) the activation portion or activation part. The cylindrical portion of the brake activator is preferably a hollow cylindrical portion. The cylindrical portion is preferably arranged coaxially with respect to the first operation unit and to the second operation unit. The cylindrical portion of the brake activator may also be arranged coaxially with respect to the cylindrical portion of the static base component. In a radial direction, the cylindrical portion of the brake activator is preferably arranged (at least in portions) between the first operation unit and the static base component, in particular between a shaft portion of the first wire drum or the first shaft and the cylindrical portion of the static base component. The provision of the cylindrical portion of the brake activator and the coaxial arrangement of the first and second operation units, the cylindrical portion of the brake activator and the cylindrical portion of the static base component advantageously makes assembly of the endoscope quite easy, since the mentioned parts simply can be inserted or put into each other along one single axis.

It may be provided that the first brake part comprises a first cone-shaped engagement surface, and the brake activator is configured to activate braking or locking a rotation of the first operation unit via an engagement of the first cone-shaped engagement surface of the first brake part with (a cone-shaped engagement surface of) the first operation unit. Preferably, the engagement is a frictional engagement. However, the present disclosure is not limited to the engagement being solely a frictional engagement. E.g., there may be provided—alternatively or in addition—some kind of geometrical lock or form lock between the touching engagement surfaces. E.g., there may be provided small bumps which interlock but are easy to overcome.

It may be provided that the second brake part comprises a second cone-shaped engagement surface, and the brake activator is configured to activate braking or locking a rotation of the second operation unit via an engagement of the second cone-shaped engagement surface of the second brake part with (a cone-shaped engagement surface of) the second operation unit. Preferably, the engagement is a frictional engagement. Alternatively or in addition there may be provided a geometrical or form locking engagement.

The first brake part may comprise the first cone-shaped engagement surface and the second brake part comprises the second cone-shaped engagement surface, and the brake activator is configured to (simultaneously) active braking or locking both a rotation of the first operation unit via an engagement of the first brake part having the first cone-shaped engagement surface with (the cone-shaped engagement surface of) the first operation unit and a rotation of the second operation unit via an engagement of the second brake part having the second cone-shaped engagement surface with (the cone-shaped engagement surface of) the second operation unit. It should be understood that a cone-shaped engagement surface is a surface with a diameter that increases along an axial direction. The surface may comprise texturing, as described below, and may have the shape of a truncated cone.

The first brake part, in particular its first cone-shaped engagement surface, may be flexible, i.e. may have a certain flexibility so as to be able to adapt to the engagement surface of the first operation unit, in particular of the first manually operable element. The first brake part may be an integral plastic or polymer part made of one single material, e.g. a thermoplastic material, preferably manufactured in a molding process, e.g. injection molding. Alternatively, the first brake part may be an integral plastic or polymer part made of two different materials, preferably manufactured in a 2K (injection) molding process. In this case, e.g. a surface or portion of the first brake part having the engagement surface which is to be brought into engagement with the engagement surface of the first operation unit, in particular of the first manually operable element may be made of a more flexible material, e.g. a thermoplastic elastomer (TPE) material, compared to a remainder of the first brake part, which may be made of a thermoplastic material. It is also conceivable to provide the first cone-shaped engagement surface of the first brake part with slices, so that a plurality of resilient engagement portions are provided which via the engagement with the engagement surface of the first operation unit, in particular of the first manually operable element are flexed into a compressed state and which are resiliently striving into an expanded state.

The second brake part, in particular its second cone-shaped engagement surface, may be flexible, i.e. may have a certain flexibility so as to be able to adapt to the engagement surface of the second operation unit, in particular of the second manually operable element. The second brake part may be an integral plastic or polymer part made of one single material, e.g. a thermoplastic material, preferably manufactured in a molding process, e.g. injection molding. Alternatively, the second brake part may be an integral plastic or polymer part made of two different materials, preferably manufactured in a 2K (injection) molding process. In this case, e.g. a surface or portion of the second brake part having the engagement surface which is to be brought into engagement with the engagement surface of the second operation unit, in particular of the second manually operable element may be made of a more flexible material, e.g. a thermoplastic elastomer (TPE) material, compared to a remainder of the second brake part, which may be made of a thermoplastic material. It is also conceivable to provide the second cone-shaped engagement surface of the second brake part with slices, so that a plurality of resilient engagement portions are provided which via the engagement with the engagement surface of the second operation unit, in particular of the second manually operable element are flexed into a compressed state and which are resiliently striving into an expanded state.

Providing the first brake part and/or the second brake part with a specific flexibility advantageously makes it possible that the first brake part and/or the second brake part, in particular their engagement surfaces, may adapt to the respective engagement surfaces of the first and second operation units, in particular of the first and second manually operable elements, which are usually made of a rather less flexible, solid (polymer/plastic) material. Therefore, misalignment between the respective engagement surfaces may be prevented or eliminated.

A cone-angle, i.e an angle of the cone of the first cone-shaped engagement surface of the first brake part is preferable in a range between 15° and 90°. In case of low brake torque requirements, the angle may be 90°, which means that the first brake part is not cone-shaped, but flat. In such a case a flat engagement surface of the first brake part may engage a flat engagement surface of the first operation unit, in particular of the the first manually operable element. Providing a cone-angle of at least 15° advantageously avoids self-locking when the first brake part engages the first operation unit, in particular the first manually operable element.

A cone-angle, i.e. an angle of the cone of the second cone-shaped engagement surface of the second brake part is preferable in a range between 15° and 90°. In case of low brake torque requirements, the angle may be 90°, which means that the second brake part is not cone-shaped, but flat. In such a case a flat engagement surface of the second brake part may engage a flat engagement surface of the second operation unit, in particular of the second manually operable element. Providing a cone-angle of at least 15° advantageously avoids self-locking when the second brake part engages the second operation unit, in particular the second manually operable element.

The first brake part and the second brake part may be identical, i.e. are identical components or members. Therefore, advantageously only one part can be manufactured or produced in high numbers, which is usable both as first brake part and as second brake part. However, the first brake part and the second brake part may also be different, for example in the cone angle or length, to accommodate different dimensions of the manually operable elements and other components surrounding or being part of the brake mechanism.

Preferably, the brake activator is configured to activate braking or locking a rotation of the first operation unit via an engagement of the first brake part with the first manually operable element. The present disclosure is however not limited to said preferred embodiment. In particular, as an alternative, e.g. an engagement of the first brake part with the first wire drum may be provided.

Preferably, the brake activator is configured to activate braking or locking a rotation of the second operation unit via an engagement of the second brake part with the second manually operable element. The present disclosure is however not limited to said preferred embodiment. In particular, as an alternative, e.g. an engagement of the second brake part with the second wire drum may be provided.

The brake activator is configured to (simultaneously) activate braking or locking both a rotation of the first operation unit via an engagement of the first brake part with the first manually operable element and a rotation of the second operation unit via an engagement of the second brake part with the second manually operable element.

It is preferred according to the present disclosure to provide the engagement between the first operation unit and the first brake part and the engagement between the second operation unit and the second brake part outside of the housing of the endoscope handle or interface. Therefore, advantageously the first brake part and the second brake part may be arranged outside of the housing of the endoscope handle or interface, which leads to less installation space being required inside the housing of the endoscope handle or interface.

Preferably, the first brake part is arranged in a first recess provided in the first manually operable element. The first recess may form an engagement surface. The first brake part is preferably in (frictional) engagement with the first recess, when the brake activator is in the brake-on position. In this case an engagement surface of the first brake part may engage the engagement surface of the first recess. According, the first recess may be cone-shaped and may comprise a cone-shaped engagement surface, the first brake part may comprise a cone-shaped engagement surface, and the cone-shaped engagement surface of the first brake part may be in (frictional) engagement with the cone-shaped engagement surface of the first recess, when the brake activator is in the brake-on position.

Preferably, the second brake part is arranged in a second recess provided in the second manually operable element. The second recess may form an engagement surface. The second brake part is preferably in (frictional) engagement with the second recess, when the brake activator is in the brake-on position. In this case an engagement surface of the second brake part may engage the engagement surface of the second recess. The second recess may be cone-shaped and may comprise a cone-shaped engagement surface, the second brake part may comprise a cone-shaped engagement surface, and the cone-shaped engagement surface of the second brake part may be in (frictional) engagement with the cone-shaped engagement surface of the second recess, when the brake activator is in the brake-on position.

Preferably, the first brake part comprises the first (cone-shaped) recess and the second brake part comprises the second (cone-shaped) recess. Preferably, the first recess and the second recess are provided on or cut into surfaces of the first and second manually operable elements which are directly adjacent to each other in the assembled state of the endoscope. E.g. in particular in case the first and second manually operable elements are formed as wheels, which in an axial direction are arranged directly adjacent each other, each of the wheels may be defined to have a top surface (which is a surface farther away from the housing of the endoscope handle) and a bottom surface (which is a surface closer to the housing of the endoscope handle). In such a case, the first recess may be provided on or cut into a bottom surface of the first manually operable element or first wheel and the second recess may be provided on or cut into a top surface of the second manually operable element or second wheel. The first recess and the second recess may thus face each other. The first recess may be formed to taper towards the top surface of the first manually operable element or first wheel, and the second recess may be formed to taper towards the bottom surface of the second manually operable element or second wheel.

The first brake part may have the cone-shaped engagement surface, which tapers in a direction away from the housing of the endoscope handle or interface. The second brake part may have the cone-shaped engagement surface, which tapers in a direction towards the housing of the endoscope handle or interface.

Preferably, the first brake part is mounted in a rotationally fixed state in the static base component. I.e. a rotation of the first brake part is preferably locked or prevented by the static base component. The first brake part thus preferably cannot rotate with respect to the static base component and thus with respect to the housing of the endoscope handle or interface. The first brake part thus preferably remains rotationally static or stationary. The first brake part preferably is only movable, i.e. can be moved in an axial direction.

Preferably, the second brake part is mounted in a rotationally fixed state in the static base component. I.e. a rotation of the second brake part is preferably locked or prevented by the static base component. The second brake part thus preferably cannot rotate with respect to the static base component and thus with respect to the housing of the endoscope handle or interface. The second brake part thus preferably remains rotationally static or stationary. The second brake part preferably is only movable, i.e. can be moved in an axial direction.

By locking rotation of the first brake part and the second brake part via the static base component, the first brake part and the second brake part will remain rotationally static both in the brake-on position and in the brake-off position of the brake activator. In particular, in the brake-on position, it is thus advantageously possible to suitably brake the rotation of the first operation unit and of the second operation unit, since rotation of the first brake part and of the second brake part is prevented by the static base component.

A spring or spring element like e.g. a coil spring may be arranged (axially) between the first brake part and the second brake part. The spring or spring element preferably is configured to push the first brake part and the second brake part apart or away from each other in the axial direction. This has the specific advantage that only one (push) spring or spring element, i.e. not two, three or more, is provided which exerts its spring force both onto the first brake part and onto the second brake part, keeping the number of parts to be assembled to a minimum. It is to be understood that the present disclosure is not limited to the embodiment according to which only one spring or spring element is provided. E.g. there may be provided two springs or spring elements so that each brake part has its own spring or spring element. It is further to be understood that the provision of a spring or spring element is not essential according to the present disclosure. E.g., it may be provided that the brake activator brings the first and second brake parts into engagement with the first and second operation units in the brake-on position of the same and brings the first and second brake parts into disengagement with the first and second operation units in the brake-off position of the same without any spring or spring element being provided.

Preferably, when the brake activator is in the brake-off position, the brake activator, in particular its activation portion or part, is configured to hold the first brake part and the second brake part in defined, i.e. specific positions, in particular with a defined or specific distance with respect to each other, wherein the spring or spring element is compressed by the first and second brake parts and wherein the first and second brake parts do not engage the first and second operation units. In particular, engagement surfaces of the first and second brake parts do not contact or frictionally engage the respective engagement surfaces provided in the first and second operation units, in particular in the first and second manually operable elements. In other words, when the brake activator is in the brake-off position, the brake activator, in particular its activation portion or part, pulls together and holds the first and second brake parts locked in place axially with the spring or spring element compressed between them.

Preferably, when the brake activator is switched or rotated or turned from the brake-off position to the brake-on position, the brake activator, in particular its activation portion or part, is configured to enable axial movement of the first brake part and the second brake part with respect to each other, so that the spring or spring element may press or push the first brake part and the second brake part apart or away from each other in the axial direction and may press or push the first brake part against the first operation unit, in particular against the first manually operable element and the second brake part against the second operation unit, in particular against the second manually operable element. In other words, the first brake part and the second brake part are preferably axially translated via the spring or spring element provided between the first brake part and the second brake part, until the first brake part engages the first operation unit, in particular the first manually operable element and the second brake part engages the second operation unit, in particular the second manually operable element. The spring or spring element preferably presses the rotationally static or stationary first and second brake parts against the rotating or rotationally movable first and second operation units, in particular the manually operable elements, resulting in a frictional engagement and thus in a braking of the first and second operation units, in particular of the first and second manually operable elements. An axial movement of the first brake part and of the second brake part is thus preferably stopped when the first brake part and the second brake part engage the first and second operation units, in particular the first and second manually operable elements, in particular the wheels, i.e. is preferably not stopped by the (activation part/portion of the) brake activator.

Preferably, the brake activator, in particular its activation portion or part formed by or comprising the cylindrical portion, comprises at least one cam surface portion enabling, when the brake activator is switched, in particular rotated from the brake-off position to the brake-on position, axial movement of the first brake part and of the second brake part. Preferably, two cam surface portions are provided, which may be arranged diametrically opposed on an outer circumferential surface of the cylindrical portion of the brake activator.

Preferably, when the brake activator is switched, in particular rotated, from the brake-off position to the brake-on position a spring pretension of the spring or spring element is released, and when the brake activator is switched, in particular rotated, from the brake-on position to the brake-off position the spring or spring element is tensioned. The brake activator thus advantageously has a lower resistance when switched from the brake-off position to the brake-on position and a higher resistance when switched from the brake-on position to the brake-off position. This advantageously reduces a likelihood that the brake activator is accidentally brought or switched or rotated into the brake-off position, in which both operation units are freely rotatable. In particular, there may be the danger that a patient's body cavity examined by the endoscope may be injured in case of a sudden or unexpected bending of the actively bendable bending section of the endoscope. It is however also conceivable according to the present disclosure that the brake activator has a higher resistance when switched from the brake-off position to the brake-on position and a lower resistance when switched from the brake-on position to the brake-off position.

Preferably, the endoscope according to the present disclosure comprises a brake system or device having only four parts—the brake activator, the first brake part, the second brake part and the spring or spring element. When the first brake part and the second brake part are formed identically, which is preferred according to the present disclosure, only two molding tools (for the brake activator and the brake part) may be provided, which enables a reduction of costs.

The present disclosure further relates to a system comprising: an endoscope as described above; and a monitor connectable to the endoscope.

BRIEF DESCRIPTION OF THE DRAWINGS

The disclosure is explained in more detail below using preferred embodiments and referring to the accompanying figures.

FIG. 8 is a front view of a portion of the brake activator with installed brake parts and spring element in-between;

FIG. 9 is a schematic view illustrating an actuation of the braking/locking mechanism;

FIG. 10 is a perspective view of the brake activator, the brake parts and the spring element being installed in a static base component;

The figures are schematic in nature and serve only to understand the disclosure. Identical elements are marked with the same reference signs.

DETAILED DESCRIPTION

Figures 1, 2, 3:
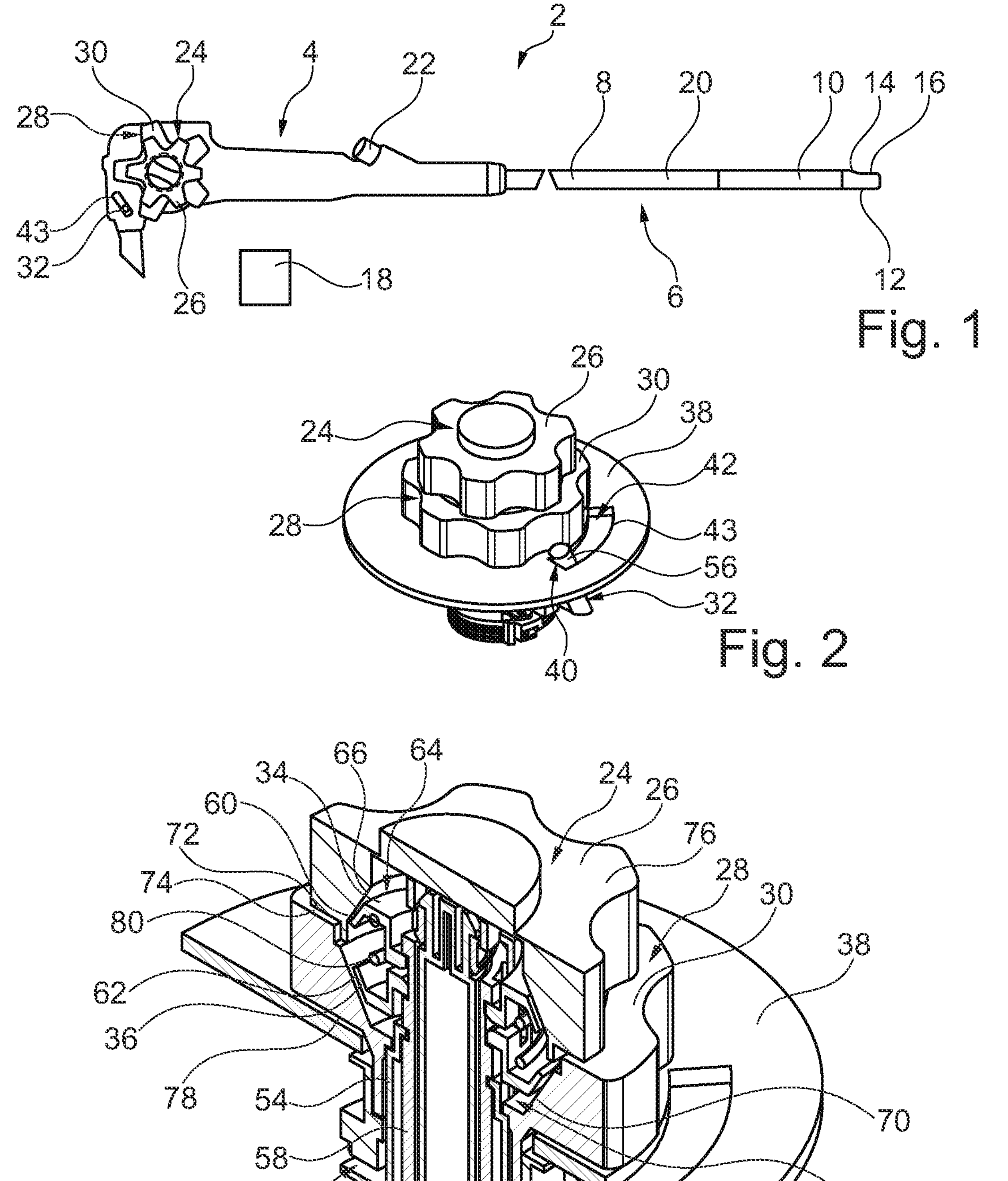
FIG. 1 is a side view of an endoscope according to the present disclosure.
FIG. 2 is a perspective view of a portion of an endoscope handle of the endoscope showing in particular a steering and braking/locking mechanism.
FIG. 3 is a perspective cross-sectional view of the portion of the endoscope handle shown in FIG. 2.

In FIG. 1, an endoscope 2 is shown. The endoscope 2 is preferably a single-use miniature/baby endoscope, such as a cholangioscope. The endoscope 2 comprises a proximal endoscope handle 4 designed to be held by an operator and being configured to accommodate operating parts of the endoscope 2. The endoscope 2 further comprises an insertion cord 6 configured to be inserted into a patient's body cavity. The insertion cord 6 comprises an insertion tube 8, an actively bendable bending section 10 and a distal tip unit 12, which extend in this order from the endoscope handle 4. In the distal tip unit 12 a light emitting device 14 and an imaging device 16 are accommodated, so that the patient's body cavity can be illuminated and inspected. Pictures/videos captured by the imaging device 16 can be shown on a monitor 18 provided separately from and connectable with the endoscope 2. The endoscope 2 has an internal working channel 20, which is accessible via an access port 22 and via which a surgical tool or instrument can be guided into the patient's body cavity.

The endoscope handle 4 comprises a steering mechanism including a first operation unit 24 having a first manually operable element 26 and a second operation unit 28 having a second manually operable element 30 arranged coaxially with respect to each other. The first manually operable element 26 and the second manually operable element 30 are both formed as handle wheels in FIG. 1. When the first manually operable element 26 is rotated by an operator, the actively bendable bending section 10 is bent in a first bending plane (e.g. in an up-and-down direction). When the second manually operable element 30 is rotated by the operator, the actively bendable bending section 10 is bent in a second bending plane (e.g. in a left-and-right direction). It may also be the other way round, i.e. rotating the first manually operable element 26 may lead to a bending in the left-and-right direction and rotating the second manually operable element 30 may lead to a bending in the up-and-down direction. The first bending plane is preferably perpendicular to the second bending plane. The endoscope 2 shown in FIG. 1 is thus a two-plane bending or four-way bending endoscope.

As can be also seen in FIG. 1 the endoscope handle 4 comprises a braking or locking mechanism including a manually operable brake activator 32. The brake activator 32 is configured to activate braking or locking both a rotation of the first operation unit 24 via an engagement of a first brake part 34 with the first operation unit 24 and a rotation of the second operation unit 28 via an engagement of a second brake part 36 with the second operation unit 28. The endoscope 2 according to the present disclosure thus comprises a double brake, via which rotation of the first operation unit 24 and of the second operation unit 28 can be simultaneously braked or locked as will be described in detail in the following.

FIG. 2 shows a perspective view of a portion of the endoscope handle 4, in particular of the steering mechanism and of the braking or locking mechanism according to the present disclosure. In particular, a portion of a housing 38 of the endoscope handle 4 is shown, where the first manually operable element 26, the second manually operable element 30 and the brake activator 32 are provided. The first manually operable element 26 and the second manually operable element 30 are arranged outside with respect to the housing 38 of the endoscope handle 4. In an axial direction the first manually operable element 26 is arranged next to the second manually operable element 30, wherein the second manually operable element 30 is closer to the housing 38 of the endoscope handle 4 and the first manually operable element 26 is farther away from the housing 38 of the endoscope handle 4. The first manually operable element 26 and the second manually operable element 30 can be rotated by the operator in order to effect bending of the actively bendable bending section 10. The brake activator 32 is in portions arranged outside with respect to the housing 38 of the endoscope handle 4 so as to be operable by the operator.

The brake activator 32 is shown in a brake-off position 40 in FIG. 2 and can be rotated by the operator over a rather small angular range, e.g. over less than 90°, between the brake-off position 40 and a brake-on position 42, in particular in an opening 43 provided in the housing 38 of the endoscope handle 4. In the brake-off position 40 of the brake activator 32 braking or locking the rotation of the first operation unit 24 and of the second operation unit 28 is deactivated, i.e. bending of the bending section 10 can be effected by the operator and the first manually operable element 26 and the second manually operable element 30 are freely rotatable, i.e. without being locked or braked. In the brake-on position 42 of the brake activator 32 braking or locking the rotation of the first operation unit 24 and of the second operation unit 28 is activated, i.e. rotation of the first manually operable element 26 and the second manually operable element 30 is restricted so that bending of the bending section 10 stays in position and is not accidentally effected by the operator and the bending section 10 remains in a braked state. However, the brake torque applied in the braked state is preferably limited so the operator would be able to fine-tune position of the bending section 10 even in the brake-on position. Further a limited brake torque would also mean that e.g. if an endoscope 2 is accidentally withdrawn from a patient with the endoscope 2 in bent configuration with activated brake the endoscope bending section 10 could straighten out, thereby mitigating a potential risk of injury to the patient.

Figures 4, 5:
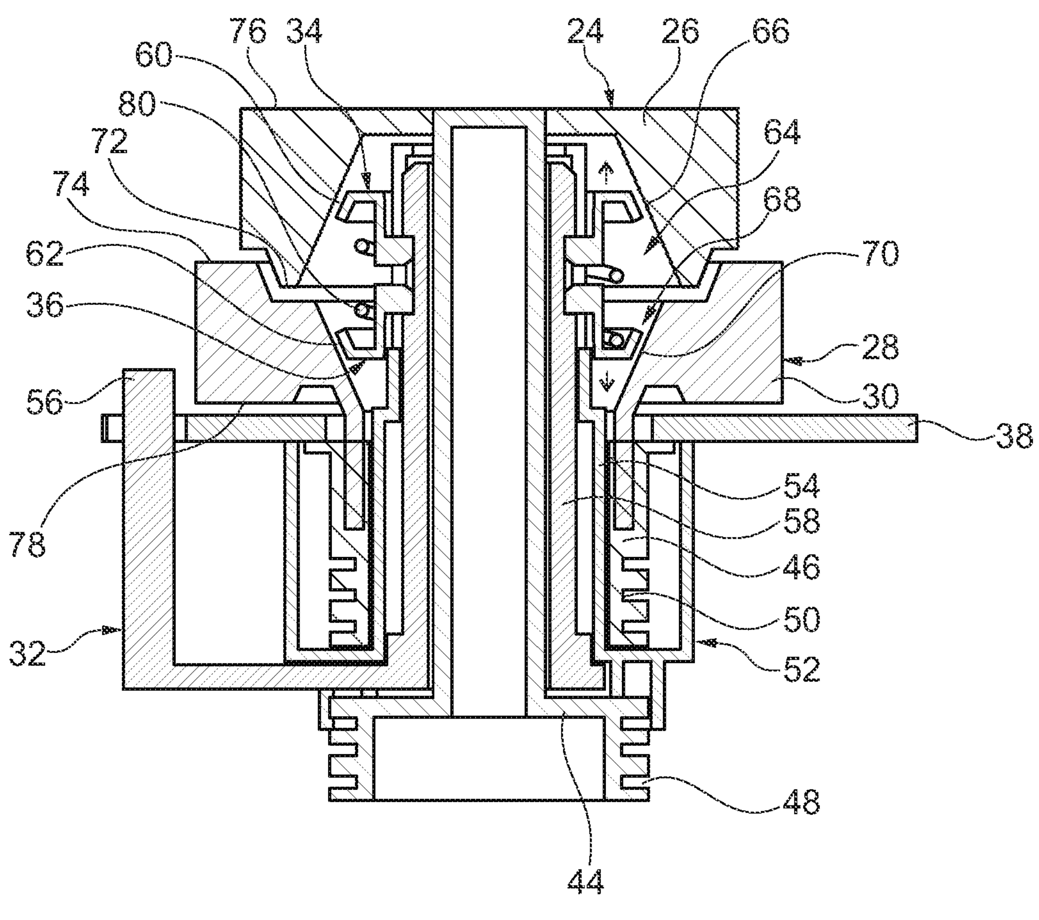
FIG. 4 is a cross-sectional view of the portion of the endoscope handle shown in FIG. 2.
FIG. 5 is an enlarged cross-sectional view of said portion showing brake parts of the braking/locking mechanism in a disengaged state.

FIG. 3 is a perspective cross-sectional view of the portion of the endoscope handle 4 shown in FIG. 2 and FIG. 4 is a cross-sectional view of the portion of the endoscope handle 4 shown in FIG. 2.

As can be seen in FIG. 3 and FIG. 4, the first operation unit 24 comprises the first manually operable element 26 and a first wire drum 44 fixed to each other via a snap connection. A rotation of the first manually operable element 26 by the operator leads directly to a rotation of the first wire drum 44 and thus to a rotation of the entire first operation unit 24. The second operation unit 28 comprises the second manually operable element 30 and a second wire drum 46 fixed to each other via a snap connection. A rotation of the second manually operable element 30 by the operator leads directly to a rotation of the second wire drum 46 and thus to a rotation of the entire second operation unit 28. Steering wires (not shown) are connected to first and second steering wire connection portions 48, 50 of the first and second wire drums 44, 46 and rotations of the first and second wire drums 44, 46 lead to pulling or releasing movements of the steering wires, effecting the bending movement of the actively bendable bending section 10. The steering wire connection portion 48, 50 are basically fixation points or portions. These fixation points or portions can be placed at any rotational position.

The second operation unit 28 is arranged radially further outside with respect to the first operation unit 24 and is arranged axially between the first manually operable element 26 and the first steering wire connection portion 48 of the first operation unit 24. In the embodiment shown in FIG. 3 and in FIG. 4 the entire second wire drum 46 is arranged inside the housing 38 of the endoscope handle 4, whereas the first wire drum 44 is at least in portions arranged outside the housing 38 of the endoscope handle 4. Both the first and second steering wire connection portions 48, 50 of the first and second wire drums 44, 46 are arranged inside the housing 38 of the endoscope handle 4 and are arranged next to each other in the axial direction, wherein the second steering wire connection portion 50 is closer to the housing 38 of the endoscope handle 4 than the first steering wire connection portion 48.

As shown in FIG. 3 and FIG. 4, the endoscope handle 4 further comprises a static base component 52, which is an integral part and which is fixedly attached to the housing 38 of the endoscope handle 4. The static base component 52 is thus a stationary or static part, i.e. is immovable with respect to the housing 38 of the endoscope handle 4. The static base component 52 comprises a hollow cylindrical portion 54, which is arranged coaxially with respect to the first operation unit 24 and the second operation unit 28. The first operation unit 24 is connected to the static base component 52 and is rotatably mounted on a radially inner side of the hollow cylindrical portion 54 of the static base component 52. The second operation unit 28 is connected to the static base component 52 and is rotatably mounted on a radially outer side of the hollow cylindrical portion 54 of the static base component 52.

The brake activator 32 is an integral part and comprises a brake lever portion 56 (shown e.g. in FIG. 2 and FIG. 4), which is operable by the operator, and a hollow cylindrical activation portion 58, which is arranged coaxially with respect to the first operation unit 24, the second operation unit 28 and the hollow cylindrical portion 54 of the static base component 52. In a radial direction the hollow cylindrical activation portion 58 of the brake activator 32 is arranged between a shaft portion of the first wire drum 44 of the first operation unit 24 and the hollow cylindrical portion 54 of the static base component 52. The hollow cylindrical activation portion 58 of the brake activator 32 is configured to activate braking or locking both a rotation of the first manually operable element 26 via an engagement of a first brake part 34 with the first manually operable element 26 of the first operation unit 24 and a rotation of the second manually operable element 30 via an engagement of the second brake part 36 with the second manually operable element 30 of the second operation unit 28.

The first brake part 34 comprises a first cone-shaped brake part engagement surface and the second brake part 36 comprises a second cone-shaped brake part engagement surface 62. The first manually operable element 26 comprises a first recess 64 having a first cone-shaped recess engagement surface 66. The second manually operable element 30 comprises a second recess 68 having a second cone-shaped recess engagement surface 70. In particular, the first recess 64 is provided/cut into a bottom surface 72 of the first manually operable element 26 and the second recess 68 is provided/cut into a top surface 74 of the second manually operable element 30. The first recess 64 and the second recess 68 thus face each other. The first recess 64 is formed to taper towards a top surface 76 of the first manually operable element 26 and the second recess 68 is formed to taper towards a bottom surface 78 of the second manually operable element 30. The first cone-shaped brake part engagement surface 60 of the first brake part 34 tapers in a direction away from the housing 38 of the endoscope handle 4 and the second cone-shaped brake part engagement surface 62 tapers in a direction towards the housing 38 of the endoscope handle 4. When the brake activator 32 is in the brake-on position 42, the first cone-shaped brake part engagement surface 60 of the first brake part 34 is in frictional engagement with the first cone-shaped recess engagement surface 66 of the first recess 64 and the second cone-shaped brake part engagement surface 62 of the second brake part 36 is in frictional engagement with the second cone-shaped recess engagement surface 70 of the second recess 68. When the brake activator 32 is in the brake-off position 40, there is no frictional engagement between the respective engagement surfaces 60, 62, 66, 70.

The first brake part 34 and the second brake part 36 are identical parts. Both the first brake part 34 and the second brake part 36 are mounted in a rotationally fixed state in the static base component 52, in order to prevent a rotation of the first brake part 34 and of the second brake part 36. The first brake part 34 and the second brake part 36 can therefore only be moved in an axial direction. A coil spring 80, which is an example of a spring element according to the present disclosure, is arranged axially between the first brake part 34 and the second brake part 36. The coil spring 80 basically pushes the first brake part 34 and the second brake part 36 apart from each other in the axial direction. When the brake activator 32 is in the brake-off position 40, the brake activator 32, in particular its hollow cylindrical activation portion 58, holds the first brake part 34 and the second brake part 36 in a specific distance with respect to each other. In this state the coil spring 80 is compressed by the first and second brake parts 34, 36 and the first and second cone-shaped brake part engagement surfaces 60, 62 of the first and second brake parts 34, 36 do not frictionally engage the respective first and second cone-shaped recess engagement surfaces 66, 70 provided in the first and second manually operable elements 26, 30. When the brake activator 32 is rotated from the brake-off position 40 to the brake-on position 42, the brake activator 32, in particular its hollow cylindrical activation portion 58, enables axial movement of the first brake part 34 and the second brake part 36 with respect to each other. The coil spring 80 pushes the first brake part 34 and the second brake part 36 apart from each other in the axial direction as indicated by the arrows so that the first brake part 34 is pushed with its first cone-shaped brake part engagement surface 60 against the first cone-shaped recess engagement surface 66 of the first manually operable element 26 and that the second brake part 36 is pushed with its second cone-shaped brake part engagement surface 62 against the second cone-shaped recess engagement surface 70 of the second manually operable element 30. When the coil spring 80 presses the rotationally stationary first and second brake parts 34, 36 against the rotationally movable first and second manually operable elements 26, 30, braking of the first and second operation units 24, 28 is achieved as will be explained in more detail below.

Figure 6:
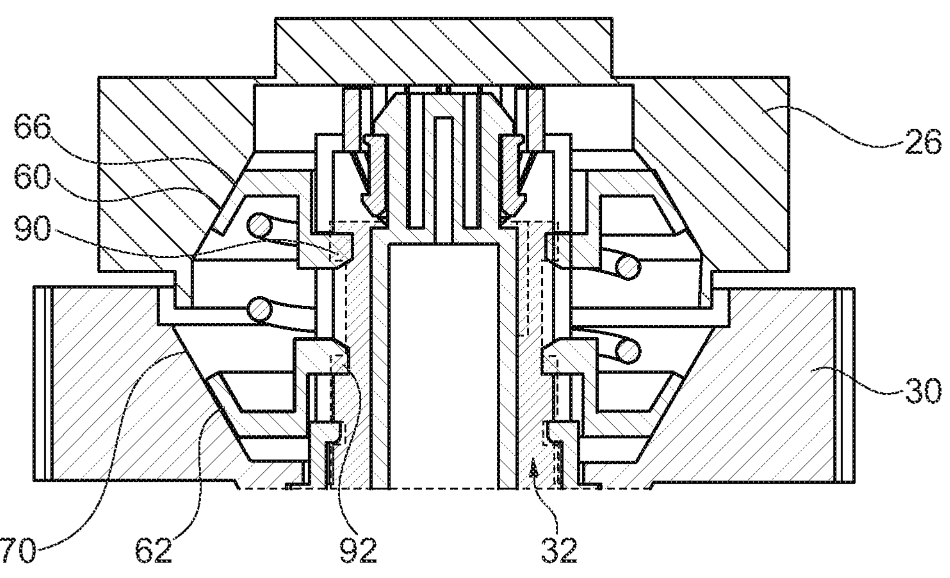
FIG. 6 is an enlarged cross-sectional view of said portion showing the brake parts of the braking/locking mechanism in an engaged state.

FIG. 5 and FIG. 6 show enlarged cross-sectional views of components of the double brake according to the present disclosure, which are arranged outside the housing 38 of the endoscope handle 4. Thereby FIG. 5 shows a state, in which the brake activator 32 is in the brake-off position 40, and FIG. 6 shows a state, in which the brake activator 32 is in the brake-on position 42. As can be seen in FIG. 5, in the brake-off position 40 of the brake activator 32, the first and second cone-shape brake part engagement surfaces 60, 62 are spaced from the respective first and second cone-shaped recess engagement surfaces 66, 70 of the first and second manually operable elements 26, 30. As can be seen in FIG. 6, in the brake-on position 42 of the brake activator 32, the first and second cone-shaped brake part engagement surfaces 60, 62 contact and frictionally engage the respective first and second cone-shaped recess engagement surfaces 66, 70 of the first and second manually operable elements 26, 30.

Figure 7:
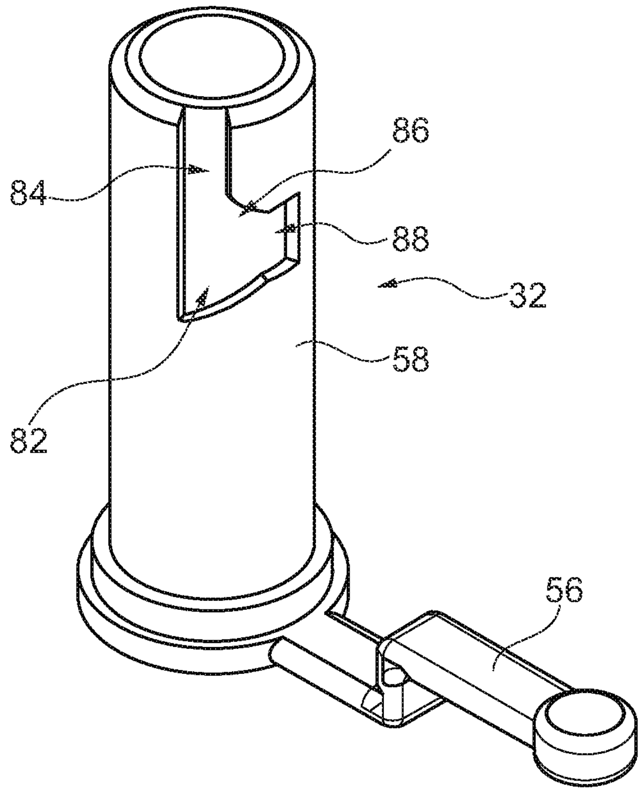
FIG. 7 is a perspective view of a brake activator of the braking/locking mechanism.
Figures 8, 9, 10:
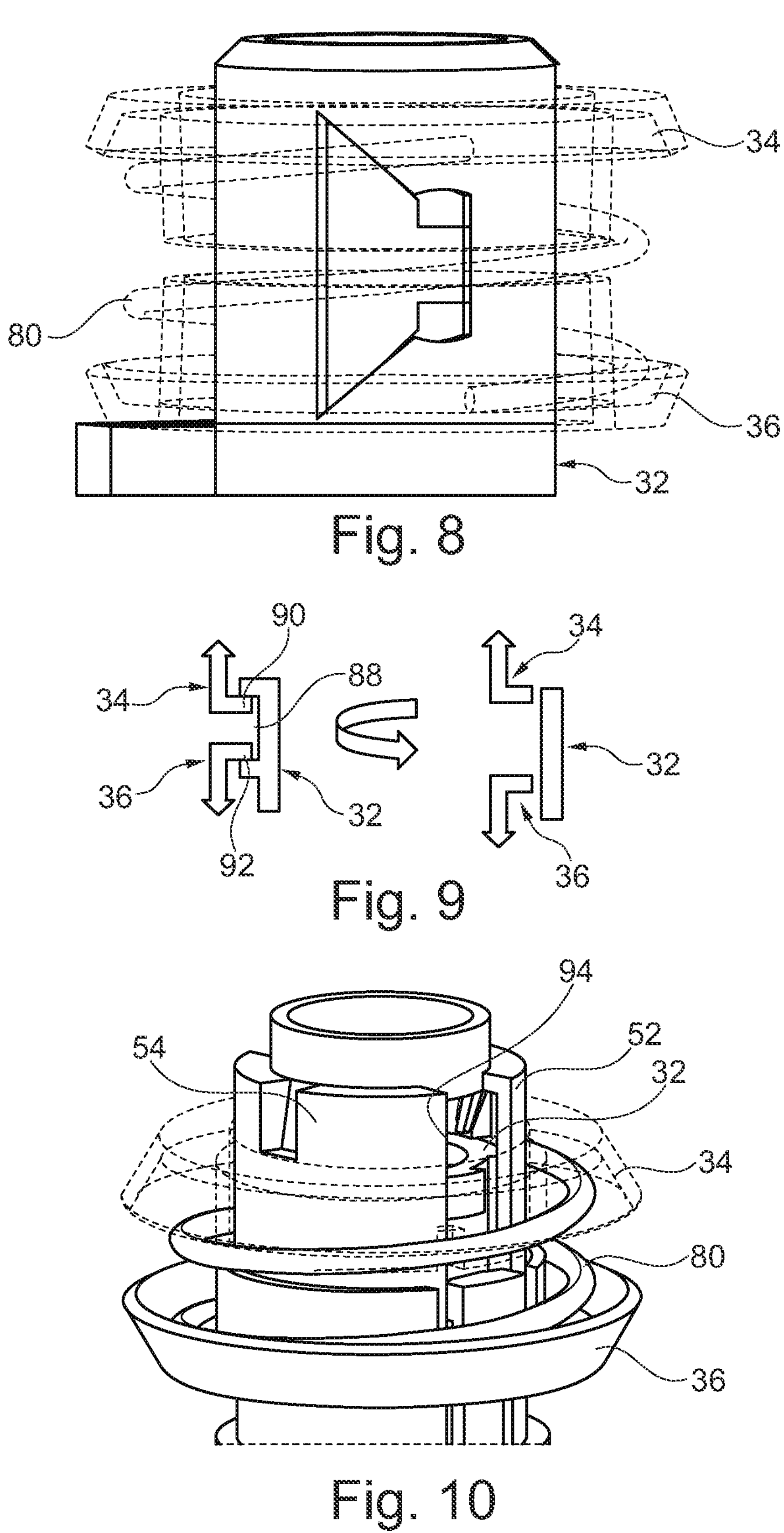

The actuation mechanism which makes it possible to simultaneously activate braking or locking both a rotation of the first manually operable element 26 and a rotation of the second manually operable element 30 is better illustrated in FIG. 7, FIG. 8, FIG. 9 and FIG. 10. FIG. 7 shows a perspective view of the brake activator 32. FIG. 8 shows a front view of a portion of the brake activator 32 with installed first and second brake parts 34, 36 and coil spring 80 in broken line for illustration. FIG. 9 is a schematic view illustrating the actuation mechanism. FIG. 10 is a perspective view (partially with broken lines for illustration) of the brake activator 32, the first and second brake parts 34, 36 as well as the coil spring 80 being installed in the static base component 52.

FIG. 7 shows the hollow cylindrical actuation portion 58 and the brake lever portion 56 of the brake activator 32. The hollow cylindrical actuation portion 58 comprises a recessed portion 82. Preferably, an identical recessed portion is provided diametrically opposed of said recessed portion 82 shown in FIG. 7. The recessed portion 82 comprises a brake part insertion portion 84, a cam surface portion 86 and a brake part holding portion 88 arranged next to each other in the circumferential direction. The brake part insertion portion 84 of the recessed portion 82 extends towards an axial end of the hollow cylindrical actuation portion 58 and enables insertion of the first and second brake parts 34, 36. The brake part holding portion 88 holds the first and second brake parts 34, 36 with a specific distance between the same, as also shown in FIG. 5. When the brake parts 34, 36 are arranged in the brake part holding portion 88, the coil spring 80 is compressed by the brake parts 34, 36 and the first and second cone-shaped brake part engagement surfaces 60, 62 do not engage the first and second cone-shaped recess engagement surfaces 66, 70. This state is shown in FIG. 8. When as shown in FIG. 9 the brake activator 32 is rotated anticlockwise, in particular via its lever portion 56, radially inward protruding portions 90, 92 of the first and second brake parts 34, 36 leave the brake part holding portion 88 and enter the cam surface portion 86 of the recessed portion 82. The cam surface portion 86 enables axial movement of the first brake part 34 and the second brake part 36 with respect to each other, which is effected by the coil spring 80. Axial movement of the first brake part 34 and the second brake part 36 is stopped in the cam surface portion 86 when the first and second cone-shaped brake part engagement surfaces 60, 62 engage the first and second cone-shaped recess engagement surfaces 66, 70. As shown in FIG. 10, the static base component 52, in particular its hollow cylindrical portion 54 comprises an opening 94, which enables insertion of the first and second brake parts 34, 36 into the static base component 52 and into the brake activator 32. The radially inward protruding portions 90, 92 of the first and second brake parts 34, 36 are accommodated in said opening 94 such that the first and second brake parts 34, 36 cannot rotate relative to the static base component 52.

Figures 11, 12:
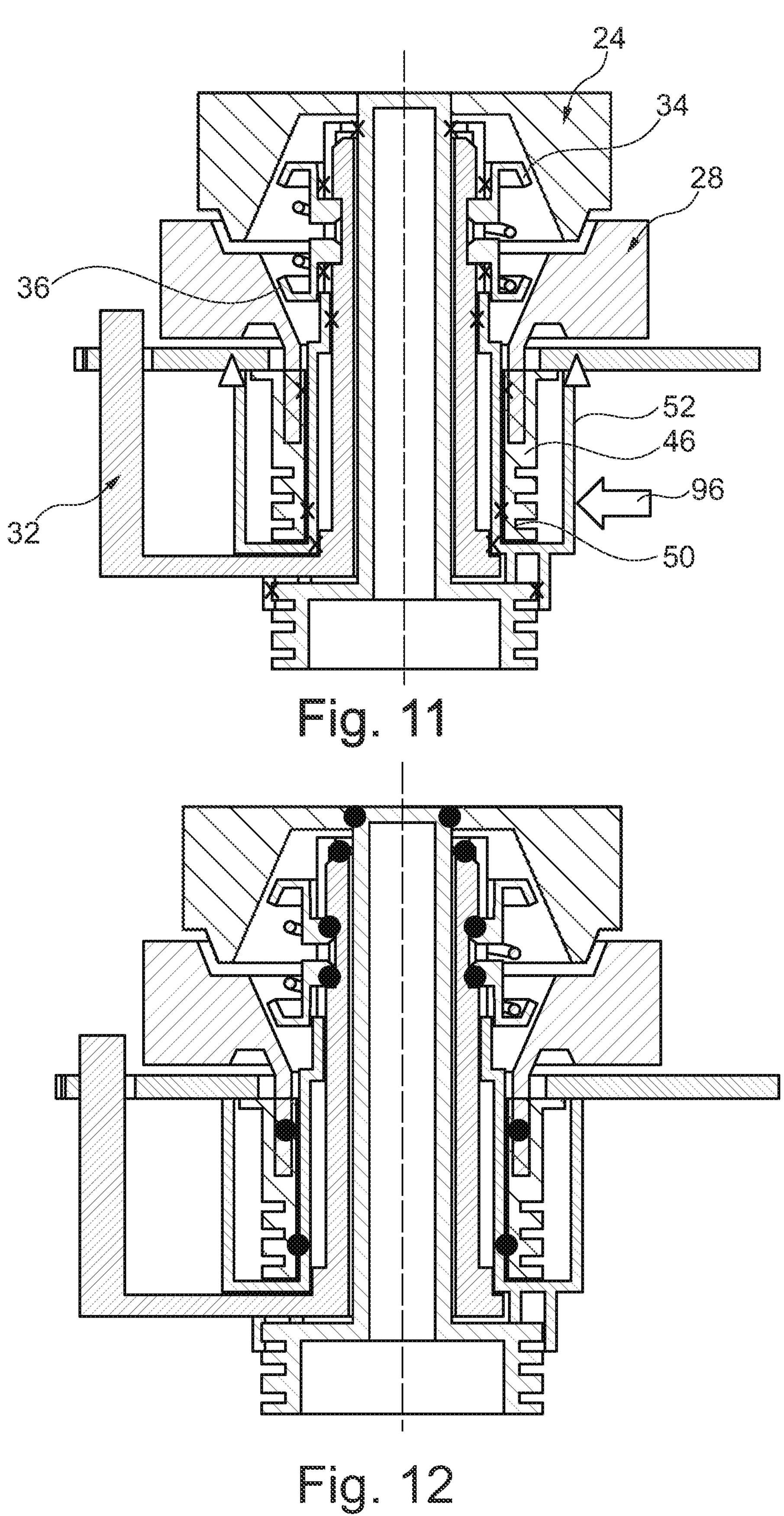
FIG. 11 shows the cross-sectional view of FIG. 4 with marked bearing interfaces.
FIG. 12 shows the cross-sectional view of FIG. 4 with marked snap interfaces.

FIG. 11 corresponds essentially to FIG. 4 and shows bearing interfaces x between the static base component 52 and the first operation unit 24, the second operation unit 28, the brake activator 32 and the first and second brake parts 34, 36. It is to be understood that the static base component 52 serves as a static or stationary reference part for the mentioned movable parts, i.e. for the first operation unit 24, the second operation unit 28, the brake activator 32 and the first and second brake parts 34, 36. An arrow 96 shown in FIG. 11 marks an opening in the static base component 52 which serves for introducing the steering wires into the steering wire connection portion 50 of the second wire drum 46. FIG. 12 also corresponds essentially to FIG. 4 and shows snap interfaces marked by a solid circle.

Figures 13, 14:
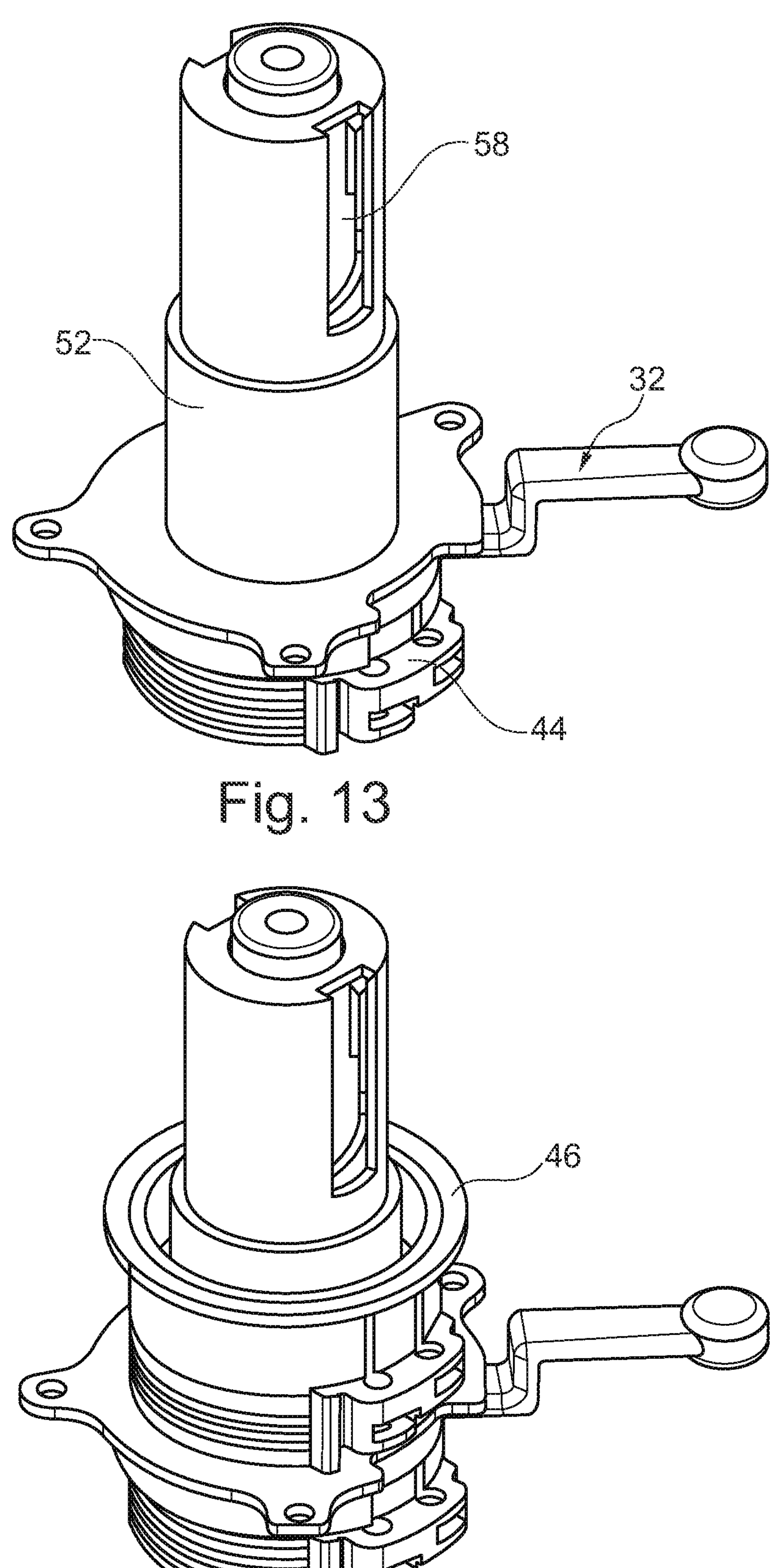
FIG. 13 is a perspective view illustrating a first assembly step of the steering and braking/locking mechanism.
FIG. 14 is a perspective view illustrating a second assembly step of the steering and braking/locking mechanism.
Figure 15:
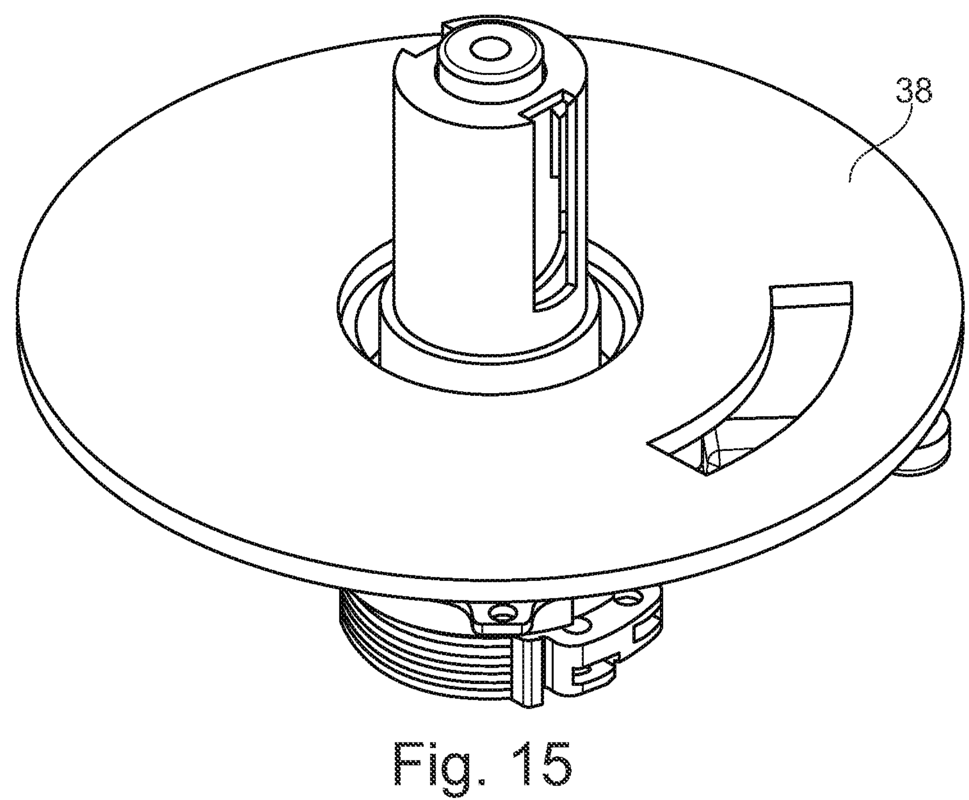
FIG. 15 is a perspective view illustrating a third assembly step of the steering and braking/locking mechanism.
Figure 16:
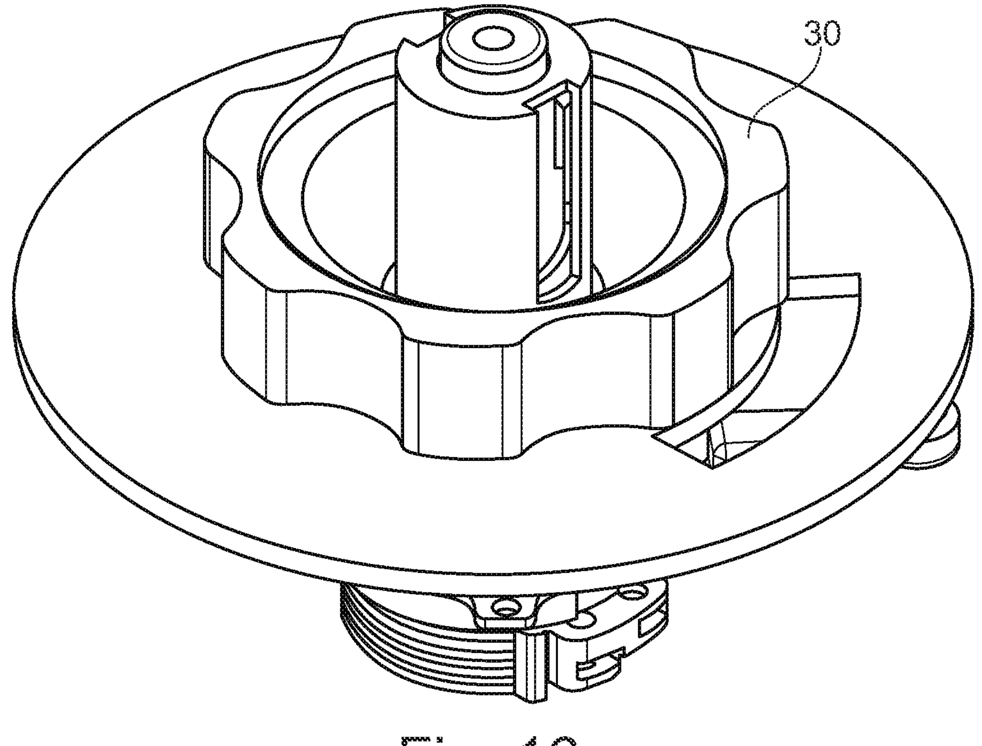
FIG. 16 is a perspective view illustrating a fourth assembly step of the steering and braking/locking mechanism.
Figure 17:
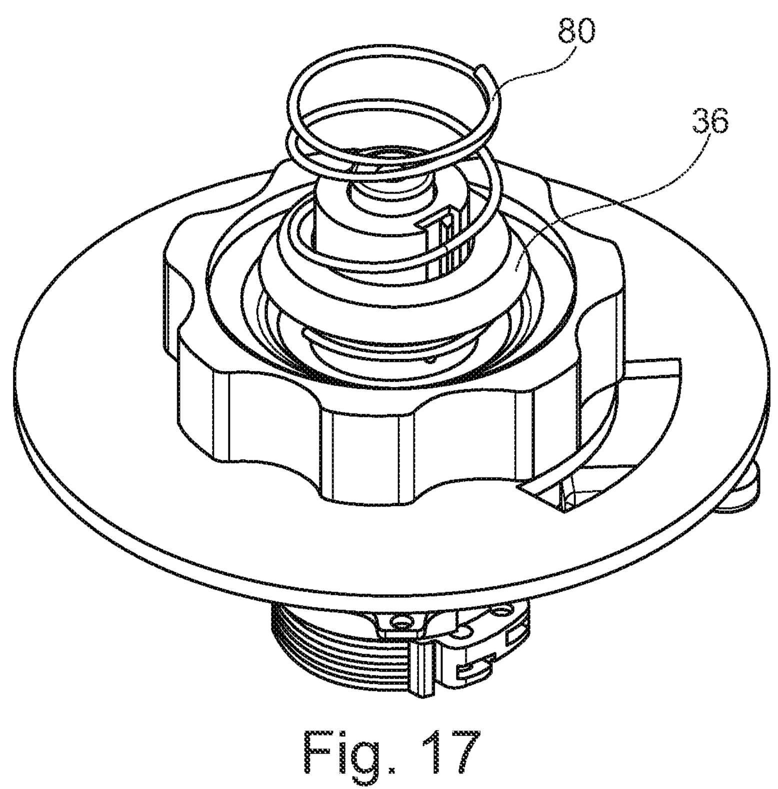
FIG. 17 is a perspective view illustrating a fifth assembly step of the steering and braking/locking mechanism.
Figure 18:
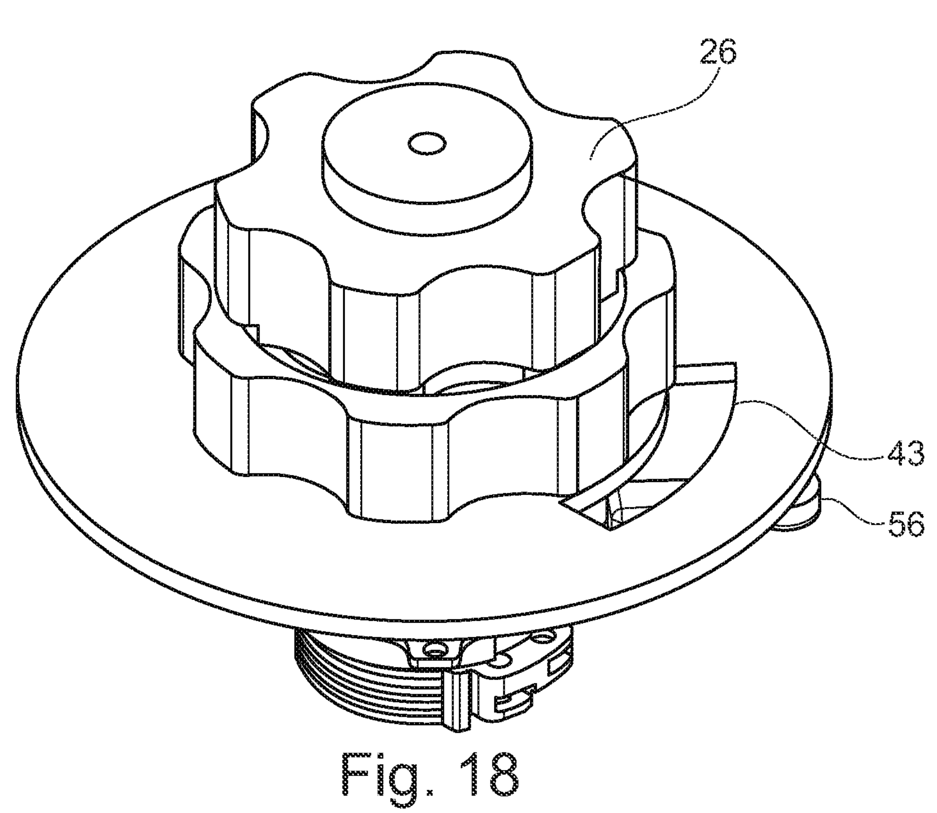
FIG. 18 is a perspective view illustrating a sixth assembly step of the steering and braking/locking mechanism and showing the brake activator in a brake-on position.

FIG. 13 to FIG. 18 illustrate an assembly of the double brake according to the present disclosure. As shown in FIG. 13, first the first wire drum 44 is inserted into the hollow cylindrical actuation portion 58 of the brake activator 32, and the assembly of the first wire drum 44 and the brake activator 32 is inserted into the static base component 52. In a next step, as shown in FIG. 14, the second wire drum 46 is added to the assembly. As shown in FIG. 15, the assembly of FIG. 14 is in a next step attached to the housing 38 (a portion again schematically illustrated as a disc) of the endoscope handle 4. Then, as shown in FIG. 16, the second manually operable element 30 is attached, in particular snapped, (on)to the second wire drum 46. In a next step, as shown in FIG. 17, the second brake part 36 and the coil spring 80 are added to the assembly shown in FIG. 16. In a final step and as shown in FIG. 18, the assembly of the double brake is completed by adding the first brake part 34 and the first manually operable element 26 to the assembly shown in FIG. 17. The first manually operable element 26 is in particular attached (on)to the first wire drum 44. The first manually operable element 26 may be attached with a snap connection.

Figure 19:
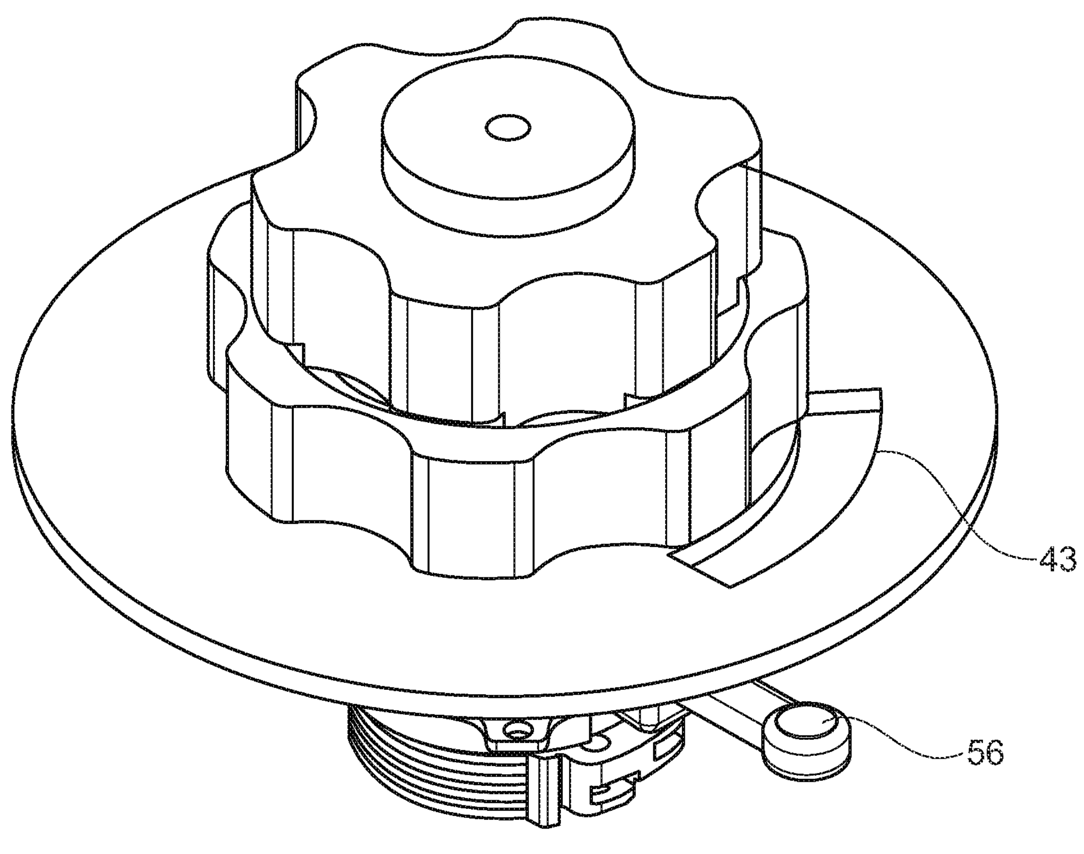
FIG. 19 is a perspective view showing the brake activator in a brake-off position.

FIG. 18 shows the brake lever portion 56 in the brake-on position 42. In FIG. 19 the brake lever portion 56 has been rotated from the brake-on position 42 to the brake-off position 40. It is to be understood that although not shown in some of the figures, the brake lever portion 56 obviously extends into the opening 43 provided in the housing 38 of the endoscope handle 4 so that the brake lever portion 56 may be operated by an operator.

The term cone should in the present context be understood to include the shape of a truncated cone. At present it is preferred that the cone is a true cone geometry with the outer surface forming a straight line from the smallest diameter at an axial end position to the largest diameter at the other axial end position, which will be the simplest version to design and produce. However cone should be understood to include a shape with a cross-section, which is not perfectly circular, such as slightly wavy or provided with ribs or grooves, and further the cone surface may bulge, e.g. so that the outer surface does not form a straight line from an axial end position to the other axial end position, but instead a curved line, such as a circular section or a number of circular sections, a combination of straight lines with different gradient, or a combination of curved and straight lines. The combination of ribs and/or grooves on mating cones could provide an extra geometrical constraint to be overcome in the brake-on position, i.e. a higher amount of braking.

The angles of any two cone elements, i.e. the first and second or third and fourth, may be the same or the angles may differ slightly. This could further increase braking function in practice, as the mating cones could be designed to ensure contact at the largest diameter, also in case of slight misalignment or variance in production. Additionally disengagement of the brake may be facilitated.

The amount of braking can be tailored to the specific preferences by e.g. the choice of spring constant, material (friction coefficient) or angle of the cones (braking cone elements).

At present an amount of braking considered relevant, for e.g. a cholangoscope, is in the order of 25-250 Nmm, such as 50-200 Nmm, for example 80-120 Nmm.

A positioning interface, or interface, functions to control the position of the insertion cord. The handle 2 is an example of a positioning interface and, unless stated otherwise, the terms are used interchangeably. The positioning interface also functions to provide the steering controls, e.g. knobs, levers, buttons, and the like, to steer the field of view of the camera and the elevator controls. Alternatively, a different positioning interface can be provided that is connected to the insertion cord and is detachably connected to a robotic arm. The insertion cord thus extends from the robotic arm, and the intrusive medical device is detachable from the robotic arm. The robotic arm responds to signals, including voice commands from an operator, to rotate, translate, and otherwise position the proximal end of the insertion cord, as an operator would do manually. The positioning interface can include control actuators, including manual control actuators. Alternatively or additionally, control actuators can be provided in or on the robotic arm or by the robotic system including the robotic arm, thereby potentially reducing the cost of the intrusive medical device. Example control actuators include single axis actuators, including linear motion actuators. A linear motion actuator may comprise a threaded rod coupled to a threaded nut portion, in which a motor rotates the rod to translate the nut portion.

The monitor 18 may also be referred to as a video processing apparatus (VPA) including a housing enclosing and supporting a display screen, a video processing circuit, and an endoscope interface configured to communicate with the camera at the distal tip. The VPA allows an operator to view an image captured by the image sensor of the camera.

Variations of the VPA can be provided. For example, it might not be desirable to provide a video display screen with a touch screen, or it might be desirable to omit a display screen altogether. Omission of the display screen might be beneficial to take advantage of evolving video display technologies which improve resolution and reduce cost. Provision of exchangeable medical device interfaces allows for adoption of evolving image sensor and endoscope technologies, thus use of existing or future-developed external video displays could allow presentation of higher resolution or otherwise improved video. Use of external video displays could also leverage existing capital investments.

In all embodiments, the endoscope may be disposable and may not be intended to be cleaned and reused. Alternatively the endoscope may, in all embodiments, be re-usable. In some variations of the present embodiment, the endoscope and the VPA comprise wireless transceivers to exchange image data and configuration data. The endoscope may comprise a battery to power the image sensor and the LEDs.

The video processing circuit of the VPA is operable to receive image data, present a graphical user interface to allow a user to manipulate image data with a touch screen, and, optionally, output a video signal to allow remote viewing of the images presented with the touch screen. A separate, potentially remote, display screen may also be connected to the endoscope via the VPA, which may include or omit the display screen. Medical device interfaces include cable sockets and circuits to compatibilize the signals from the image sensors, for example. Thus, a particular type of endoscope is matched with a corresponding medical device interface and the VPA can thus enable use of different endoscope technologies. In other words, the VPA or monitor is customized to work with endoscope. The medical device interfaces may also include isolation amplifiers to electrically isolate the video signal, and a power output connector to provide power to the endoscope for the image sensor and the LEDs. The medical device interfaces may also include a serial to parallel converter circuit to deserialize the video signals of endoscopes that generate serial signals, for example serial analog video signals. The medical device interfaces may also include a configuration connector to output image sensor configuration parameters such as image inversion, clock, shutter speed etc.

The following items are further variations and examples of the embodiments described with reference to the figures.

1. Endoscope (2) comprising: an endoscope handle (4) or interface; and an insertion cord (6) configured to be inserted into a patient's body cavity and comprising an actively bendable bending section (10); the endoscope handle (4) or interface comprising: a first operation unit (24) having a first manually operable element (26), which when rotated by an operator causes a bending of the actively bendable bending section (10) in a first bending plane; a second operation unit (28) having a second manually operable element (30), which when rotated by the operator causes a bending of the actively bendable bending section (10) in a second bending plane; and a manually operable brake activator (32) which is configured to activate braking or locking both a rotation of the first manually operable element (26) via an engagement of a first brake part (34) with the first operation unit (24) and a rotation of the second manually operable element (30) via an engagement of a second brake part (36) with the second operation unit (28).

2. Endoscope (2) according to item 1, wherein the first brake part (34) comprises a first cone-shaped engagement surface and the second brake part (36) comprises a second cone-shaped engagement surface (62), and the brake activator (32) is configured to simultaneously activate braking or locking both a rotation of the first operation unit (24) via an engagement of the first brake part (34) having the first cone-shaped engagement surface with a cone-shaped engagement surface (66) of the first operation unit (24) and a rotation of the second operation unit (28) via an engagement of the second brake part (36) having the second cone-shaped engagement surface (62) with a cone-shaped engagement surface of the second operation unit (28).

3. Endoscope (2) according to item 1 or 2, wherein the first brake part (34) and the second brake part (36) are identical parts.

4. Endoscope (2) according to any one of the preceding items 1 to 3, wherein the brake activator (32) is configured to simultaneously activate braking or locking both a rotation of the first operation unit (24) via an engagement of the first brake part (34) with the first manually operable element (26) and a rotation of the second operation unit (28) via an engagement of the second brake part (36) with the second manually operable element (30).

5. Endoscope (2) according to any one of the preceding items 1 to 4, wherein the first brake part (34) is arranged in a first recess (64) provided in the first manually operable element (26) and the second brake part (36) is arranged in a second recess (68) provided in the second manually operable element (30).

6. Endoscope (2) according to any one of the preceding items 1 to 5, further comprising a static base component (52), which is a part or component fixedly attached to a housing (38) of the endoscope handle (4) or interface, wherein the first brake part (34) and the second brake part (36) are mounted in a rotationally fixed state in the static base component (52).

7. Endoscope (2) according to any one of the preceding items 1 to 6, wherein the brake activator (32) is switchable between a brake-on position (42), which is a position of the brake activator (32) in which braking or locking the rotation of the first and second operation units (24, 28) is activated, and a brake-off position (40), which is a position of the brake activator (32) in which braking or locking the rotation of the first and second operation units (24, 28) is deactivated.

8. Endoscope (2) according to item 7, wherein the brake activator (32) comprises at least one cam surface portion (86) enabling, when the brake activator (32) is switched from the brake-off position (40) to the brake-on position (42), axial movement of the first brake part (34) and of the second brake part (36).

9. Endoscope (2) according to any one of the preceding items 1 to 8, wherein a spring element (80) is arranged between the first brake part (34) and the second brake part (36), the spring element (80) being configured to push the first brake part (34) and the second brake part (36) away from each other in an axial direction.

10. Endoscope (2) according to any one of the preceding items 1 to 6, wherein the brake activator (32) is switchable between a brake-on position (42), which is a position of the brake activator (32) in which braking or locking the rotation of the first and second operation units (24, 28) is activated, and a brake-off position (40), which is a position of the brake activator (32) in which braking or locking the rotation of the first and second operation units (24, 28) is deactivated, and wherein a spring element (80) is arranged between the first brake part (34) and the second brake part (36), the spring element (80) being configured to push the first brake part (34) and the second brake part (36) away from each other in an axial direction.

11. Endoscope (2) according to item 10, wherein, when the brake activator (32) is switched from the brake-off position (40) to the brake-on position (42) a spring pretension of the spring element (80) is released, and when the brake activator (32) is switched from the brake-on position (42) to the brake-off position (40) the spring element (80) is tensioned.

12. Endoscope (2) according to item 10 or 11, wherein when the brake activator (32) is in the brake-off position (40), the brake activator (32) is configured to hold the first brake part (34) and the second brake part (36) in a specific distance with respect to each other, wherein the spring element (80) is compressed by the first and second brake parts (34, 36), and wherein the first and second brake parts (34, 36) do not engage the first and second operation units (24, 28).

13. Endoscope (2) according to any one of the preceding items 10 to 12, wherein when the brake activator (32) is switched from the brake-off position (40) to the brake-on position (42), the brake activator (32) is configured to enable axial movement of the first brake part (34) and the second brake part (36) with respect to each other, so that the spring element (80) pushes the first brake part (34) and the second brake part (36) away from each other in the axial direction and pushes the first brake part (34) against the first operation unit (24) and the second brake part (36) against the second operation unit (28).

14. Endoscope (2) according to any one of the preceding items 1 to 13, the endoscope (2) comprising a brake device having only four parts, namely the brake activator (32), the first brake part (34), the second brake part (36) and a/the spring element (80).

15. System comprising: an endoscope (2) according to any one of items 1 to 14; and a monitor (18) connectable to the endoscope (2).

The term "comprising," "including," and "having," and variations thereof, are open transition terms that specify the presence of stated features, integers, steps or components but do not preclude the presence or addition of one or more other features, integers, steps, components or groups thereof. By contrast, the term "consisting" is a closed transition term that precludes the presence or addition of one or more other features, integers, steps, components or groups thereof.

The term "preferred" and variations thereof, including "especially preferred," in connection with a feature, indicate that the feature describes an example or variation of an embodiment and, unless context requires otherwise, the feature is optional.

LIST OF REFERENCE SIGNS

2 endoscope 4 endoscope handle
6 insertion cord
8 insertion tube
10 bending section
12 distal tip unit
14 light emitting device
16 imaging device
18 monitor
20 working channel
22 access port
24 first operation unit
26 first manually operable element
28 second operation unit
30 second manually operable element
32 brake activator
34 first brake part
36 second brake part
38 housing (of endoscope handle)
40 brake-off position
42 brake-on position

43 opening
44 first wire drum
46 second wire drum
48 first steering wire connection portion (of first wire drum)
50 second steering wire connection portion (of second wire drum)
52 static base component
54 hollow cylindrical portion (of static base component)
56 brake lever portion
58 hollow cylindrical activation portion
60 first cone-shaped brake part engagement surface
62 second cone-shaped brake part engagement surface
64 first recess
66 first cone-shaped recess engagement surface
68 second recess
70 second cone-shaped recess engagement surface
72 bottom surface (of first manually operable element)
74 top surface (of second manually operable element)
76 top surface (of first manually operable element)
78 bottom surface (of second manually operable element)
80 coil spring
82 recessed portion
84 brake part insertion portion
86 cam surface portion
88 brake part holding portion
90 radially inward protruding portion (of first brake part)
92 radially inward protruding portion (of second brake part)
94 opening
96 arrow

I claim:

1. An endoscope comprising:
an insertion cord configured to be inserted into a patient's body cavity and comprising a bending section; and
a handle or interface, the insertion cord extending distally from the handle or interface, the handle or interface comprising:
a first operation unit having a first manually operable element configured to cause, when rotated, bending of the bending section in a first bending plane;
a second operation unit having a second manually operable element configured to cause, when rotated, bending of the bending section in a second bending plane;
a first brake part;
a second brake part; and
a manually operable brake activator having a longitudinal axis, the first manually operable element and the second manually operable element being concentric with the brake activator, the brake activator being configured to enable separation of the first brake part from the second brake part along the longitudinal axis, said axial separation causing engagement of the first brake part with the first operation unit and engagement of the second brake part with the second operation unit, said engagements braking rotation, respectively, of the first manually operable element and the second manually operable element.

2. The endoscope of claim 1, wherein the first brake part comprises a first cone-shaped engagement surface and the second brake part comprises a second cone-shaped engagement surface, and wherein the first operation unit comprises a cone-shaped engagement surface and the second operation unit comprises a cone-shaped engagement surface, said engagements comprising engagement of the first cone-shaped engagement surface with the cone-shaped engagement surface of the first operation unit and engagement of the second cone-shaped engagement surface with the cone-shaped engagement surface of the second operation unit.

3. The endoscope of claim 2, wherein said engagements occur simultaneously.

4. The endoscope of claim 2, wherein the first brake part and the second brake part are identical.

5. The endoscope of claim 1, wherein said engagements comprise engagement of the first brake part with the first manually operable element and engagement of the second brake part with the second manually operable element.

6. The endoscope of claim 1, wherein the first manually operable element comprises a first recess and the first brake part is positioned in the first recess, and wherein the second manually operable element comprises a second recess and the second brake part is positioned in the second recess.

7. The endoscope of claim 1, wherein the handle or interface comprises a housing, the endoscope further comprising a static base component which is an integral part of, or is fixedly attached to, the housing, and wherein the first brake part and the second brake part are rotatably mounted on the static base component.

8. The endoscope of claim 1, wherein the brake activator is switchable between a brake-on position and a brake-off position, wherein in the brake-on position the brake activator causes said engagements and in the brake-off position the brake activator does not cause said engagements.

9. The endoscope of claim 8, wherein the brake activator comprises at least one cam surface portion enabling, when the brake activator is switched from the brake-off position to the brake-on position, axial movement of the first brake part and of the second brake part.

10. An endoscope comprising:
an insertion cord configured to be inserted into a patient's body cavity and comprising a bending section; and
a handle or interface, the insertion cord extending distally from the handle or interface, the handle or interface comprising:
a first operation unit having a first manually operable element configured to cause, when rotated, bending of the bending section in a first bending plane;
a second operation unit having a second manually operable element configured to cause, when rotated, bending of the bending section in a second bending plane;
a first brake part;
a second brake part;
a spring positioned between the first brake part and the second brake part, the spring being configured to push the first brake part and the second brake part away from each other in an axial direction; and
a manually operable brake activator configured to cause engagement of the first brake part with the first operation unit and engagement of the second brake part with the second operation unit, said engagements braking rotation, respectively, of the first manually operable element and the second manually operable element,
wherein the brake activator is switchable between a brake-on position and a brake-off position, wherein in the brake-on position the brake activator causes said engagements and in the brake-off position the brake activator does not cause said engagements, and
wherein the brake activator comprises at least one cam surface portion enabling, when the brake activator is switched from the brake-off position to the brake-on position, axial movement of the first brake part and of the second brake part.

11. An endoscope comprising:

an insertion cord configured to be inserted into a patient's body cavity and comprising a bending section; and a handle or interface, the insertion cord extending distally from the handle or interface, the handle or interface comprising:

a first operation unit having a first manually operable element configured to cause, when rotated, bending of the bending section in a first bending plane;

a second operation unit having a second manually operable element configured to cause, when rotated, bending of the bending section in a second bending plane;

a first brake part; and a second brake part, and a manually operable brake activator configured to cause engagement of the first brake part with the first operation unit and engagement of the second brake part with the second operation unit, said engagements braking rotation, respectively, of the first manually operable element and the second manually operable element, wherein the brake activator is switchable between a brake-on position and a brake-off, wherein in the brake-on position the brake activator causes said engagements and in the brake-off position the brake activator does not cause said engagements, and wherein a spring is arranged between the first brake part and the second brake part, the spring being configured to push the first brake part and the second brake part away from each other in an axial direction.

12. The endoscope of claim 11, wherein the spring is tensioned responsive to the brake activator being switched from the brake-on position to the brake-off position and the tension of the spring is released responsive to the brake activator being switched from the brake-off position to the brake-on position.

13. The endoscope of claim 11, wherein when the brake activator is in the brake-off position, the brake activator holds the first brake part and the second brake part in a specific distance with respect to each other, the first brake part and the second brake part compress the spring, and the first brake part and the second brake part do not engage, respectively, the first operation unit and second operation unit.

14. The endoscope of claim 13, wherein when the brake activator is switched from the brake-off position to the brake-on position, the brake activator enables axial movement of the first brake part and the second brake part with respect to each other, so that the spring pushes the first brake part and the second brake part away from each other in the axial direction and pushes the first brake part against the first operation unit and the second brake part against the second operation unit.

15. An endoscope comprising:

an insertion cord configured to be inserted into a patient's body cavity and comprising a bending section; and a handle or interface, the insertion cord extending distally from the handle or interface, the handle or interface comprising:

a first operation unit having a first manually operable element configured to cause, when rotated, bending of the bending section in a first bending plane;

a second operation unit having a second manually operable element configured to cause, when rotated, bending of the bending section in a second bending plane;

a first brake part; and a second brake part, and a manually operable brake activator configured to cause engagement of the first brake part with the first operation unit and engagement of the second brake part with the second operation unit, said engagements braking rotation, respectively, of the first manually operable element and the second manually operable element, wherein said braking rotation, respectively, of the first manually operable element and the second manually operable element is performed by a brake device consisting of the brake activator, the first brake part, the second brake part and a spring positioned coaxially between the first brake part and the second brake part.

16. The endoscope of claim 1, wherein the first brake part comprises a first cone-shaped engagement surface;

the second brake part comprises a second cone-shaped engagement surface;

the first operation unit comprises a cone-shaped engagement surface;

the second operation unit comprises a cone-shaped engagement surface;

the first manually operable element comprises a first recess and the first brake part is positioned in the first recess;

the second manually operable element comprises a second recess and the second brake part is positioned in the second recess;

said engagements comprise engagement of the first cone-shaped engagement surface with the cone-shaped engagement surface of the first operation unit and engagement of the second cone-shaped engagement surface with the cone-shaped engagement surface of the second operation unit; and the brake activator is switchable between a brake-on position and a brake-off position, in the brake-on position the brake activator causes said engagements and in the brake-off position the brake activator does not cause said engagements.

17. The endoscope of claim 1, wherein the first brake part comprises a first cone-shaped engagement surface, wherein the first manually operable element comprises a recess comprising a cone-shaped engagement surface, said axial separation causing engagement, in the recess, of the first cone-shaped engagement surface with the cone-shaped engagement surface of the first manually operable element.

18. The endoscope of claim 17, wherein the second brake part comprises a second cone-shaped engagement surface, wherein the second manually operable element comprises a recess comprising a cone-shaped engagement surface, said axial separation causing engagement, in the recess of the second manually operable element, of the second cone-shaped engagement surface with the cone-shaped engagement surface of the second manually operable element.

19. An endoscope comprising:

an insertion cord comprising a bending section; and a handle or interface, the insertion cord extending distally from the handle or interface, the handle or interface comprising:

a first steering wheel configured to cause, when rotated, bending of the bending section in a first bending plane, the first steering wheel comprising a first recess including a cone-shaped engagement surface, a second steering wheel configured to cause, when rotated, bending of the bending section in a second bending plane, the second steering wheel comprising a second recess including a cone-shaped engagement surface, a first brake part including a first cone-shaped engagement surface;

a second brake part including a second cone-shaped engagement surface;

a spring between the first brake part and the second brake part; and a manually operable brake activator configured to enable the spring to expand and cause axial separation of the first brake part and the second brake part, wherein said axial separation causes engagements comprising:

engagement of the first cone-shaped engagement surface with the cone-shaped engagement surface of the first steering wheel in the first recess, and engagement of the second cone-shaped engagement surface with the cone-shaped engagement surface of the second steering wheel in the second recess.

20. The endoscope of claim 19, wherein the brake activator is rotatable between a brake-on position and a brake-off position, wherein in the brake-on position the brake activator causes said engagements and in the brake-off position the brake activator does not cause said engagements.

* * * * *